United States Patent
Deeley et al.

(10) Patent No.: US 11,787,760 B2
(45) Date of Patent: Oct. 17, 2023

(54) PROCESS FOR MAKING ETHERS VIA ENOL ETHERS

(71) Applicant: BP P.L.C., London (GB)

(72) Inventors: Jon Deeley, Middlesex (GB); Gareth Armitage, Middlesex (GB); Fiona Jackson, Middlesex (GB); Gregory Price, Middlesex (GB)

(73) Assignee: BP P.L.C., London (GB)

( * ) Notice: Subject to any disclaimer, the term of this patent is extended or adjusted under 35 U.S.C. 154(b) by 20 days.

(21) Appl. No.: 17/295,639

(22) PCT Filed: Nov. 5, 2019

(86) PCT No.: PCT/GB2019/053127
§ 371 (c)(1),
(2) Date: May 20, 2021

(87) PCT Pub. No.: WO2020/104768
PCT Pub. Date: May 28, 2020

(65) Prior Publication Data
US 2022/0002220 A1    Jan. 6, 2022

(30) Foreign Application Priority Data

Nov. 20, 2018 (GB) .................................. 1818905

(51) Int. Cl.
| | | |
|---|---|---|
| C07C 41/20 | (2006.01) | |
| C10M 129/16 | (2006.01) | |
| C07C 41/01 | (2006.01) | |
| C07C 41/09 | (2006.01) | |

(52) U.S. Cl.
CPC .............. *C07C 41/20* (2013.01); *C07C 41/01* (2013.01); *C07C 41/09* (2013.01); *C10M 129/16* (2013.01)

(58) Field of Classification Search
CPC ...... C10M 129/16; Y02P 20/10; C07C 41/20; C07C 41/09; C07C 41/01
See application file for complete search history.

(56) References Cited

U.S. PATENT DOCUMENTS

| | | | |
|---|---|---|---|
| 2,122,812 A | * | 7/1938 | Groll ...................... C07C 41/20 560/190 |
| 2,578,724 A | | 12/1951 | Mertzweiller |
| 4,479,017 A | | 10/1984 | Ayusawa et al. |
| 5,053,556 A | | 10/1991 | Ohnishi |
| 5,523,491 A | | 6/1996 | Egawa et al. |
| 6,087,539 A | | 7/2000 | Yamasaki et al. |
| 7,622,431 B2 | | 11/2009 | Muir |
| 2005/0198894 A1 | | 9/2005 | Migdal et al. |
| 2006/0090393 A1 | | 5/2006 | Rowland et al. |
| 2012/0271082 A1 | | 10/2012 | Jackson et al. |
| 2013/0109604 A1 | | 5/2013 | Patil et al. |

FOREIGN PATENT DOCUMENTS

| | | |
|---|---|---|
| CN | 1232444 A | 10/1999 |
| EP | 0832869 A1 | 4/1998 |
| EP | 1533362 A1 | 5/2005 |
| JP | 09095461 A * | 4/1997 |
| WO | 1995/001949 A1 | 1/1995 |
| WO | 1999/021902 A1 | 5/1999 |
| WO | 2003/099890 A1 | 12/2003 |
| WO | 2006/099250 A1 | 9/2006 |

OTHER PUBLICATIONS

International Search Report and Written Opinion of the International Searching Authority for International Application No. PCT/GB2019/053127, completed Jan. 28, 2020.

* cited by examiner

*Primary Examiner* — Rosalynd A Keys
(74) *Attorney, Agent, or Firm* — McDonnell Boehnen Hulbert & Berghoff LLP

(57) ABSTRACT

The present invention relates to a process for preparing ethers, particularly unsymmetrical ethers, and preferably ethers suitable for use as base stocks for lubricant compositions. In particular, the process involves the reaction of a branched-chain aldehyde and a branched-chain alcohol to form an enol ether and conversion of the enol ether to a saturated ether by reduction.

15 Claims, No Drawings

PROCESS FOR MAKING ETHERS VIA ENOL ETHERS

This application is a national stage application under 35 U.S.C. § 371 of International Application No. PCT/GB2019/053127, filed Nov. 5, 2019, which claims priority to Great Britain Application No. 1818905.0, filed Nov. 20, 2018, the disclosures of which are explicitly incorporated by reference herein.

The present invention relates to a process for preparing ethers, particularly unsymmetrical ethers, and preferably ethers suitable for use as base stocks for lubricant compositions. In particular, the process involves the reaction of a branched-chain aldehyde and a branched-chain alcohol to form an enol ether and conversion of the enol ether to a saturated ether by reduction.

BACKGROUND

Ether compounds are an important category of compounds which have found application in a variety of industries as functional additives (for instance, cosmetic, fuel or lubricant additives), solvents, diluents and as important precursors for other industrial and/or commercially desirable compounds. In particular, ether compounds have been found to be effective as base stocks in lubricant compositions.

Known processes for preparing ethers on an industrial scale include the reaction of an alcohol with an alkyl group having a suitable leaving group, such as a halogen (for example bromine, chlorine or iodine) or a sulfonate ester (for example mesylate or tosylate), in the presence of a base (for example potassium hydroxide or potassium tert-butoxide) and a catalyst (for example Starks' catalyst: N-Methyl-N,N,N-trioctyloctan-1-ammonium chloride). However, such processes have the disadvantage of generating corrosive halogenated or sulfonate ester intermediates.

An alternative approach to etherification which avoids the formation of these undesirable intermediates is the reaction of an alcohol with an alkene. A well-known example of such an etherification relates to the preparation of methyl or ethyl tert-butyl ether (MTBE or ETBE), which are well known fuel additives. This same approach has also been utilized more recently in the preparation of ether compounds for use in improving one or more of solubility and dispersancy of lubricating compositions, as illustrated in US 2013/0109604 (Example 3 thereof).

Another approach to the formation of ethers which avoids the formation of corrosive by-products is through conversion of acetals to the corresponding ether by hydrogenolysis. U.S. Pat. No. 5,523,491 describes the conversion of an acetal or ketal compound to the ether by means of hydrogenation in the presence of solid acidic catalyst having hydrogenating ability or a solid acid catalyst in combination with a hydrogenation catalyst. U.S. Pat. No. 4,479,017 describes a catalytic hydrogenolysis of an acetal compound with a palladium catalyst on a carbon carrier to produce an ether compound. U.S. Pat. No. 6,087,539 describes the formation of a vinyl ether polymer having a terminal ether group from the reaction of a vinyl ether polymer having a terminal acetal group with hydrogen in the presence of a solid catalyst comprising nickel and an oxide of silicon, aluminium, magnesium, titanium, zirconium and combinations thereof. WO 95/01949 describes the conversion of acetals to ethers, in particular 3-alkoxypropiaonaldehyde dialkyl acetal to the corresponding 1,3-dialkoxypropane, in the presence of a supported hydrogenation catalyst comprising at least one catalytic metal selected from Pd, Ni, Co, Pt, Rh and Ru, and a supported material selected from silica, alumina silica-alumina, alumino-silicates and carbon.

During the synthesis of the acetal, at least a twofold excess of alcohol in comparison to aldehyde is typically required. Upon reduction of the acetal to form the desired ether product, an alcohol by-product is formed, resulting in a 1:1 molar mixture of ether and alcohol in the final product. In order to obtain the ether, a further purification step is necessary. This by-product also makes the process atomically inefficient, which is undesirable.

Typically, the reduction process involves subjecting the acetal compound to hydrogen under conditions of high temperature and high pressure in the presence of a suitable hydrogenation catalyst. These conditions are known to be energy intensive.

There remains the need for alternative processes for preparing ethers which avoids forming corrosive halogenated or sulfonate ester intermediates, does not lead to the production of large amounts of by-products requiring separation and offers the possibility of using milder reaction conditions to reduce energy expenditure associated with the preparation process.

The present invention is based on the discovery by the inventors of an alternative route to ethers requiring milder reaction conditions in comparison to prior art methods. This route proceeds through the synthesis of enol ethers, for which particularly advantageous synthetic conditions have been determined.

The synthesis of enol ethers from aldehyde and alcohol starting materials has been previously disclosed in U.S. Pat. No. 5,053,556. However, it has been found by the inventors that the conditions used in U.S. Pat. No. 5,053,556 result in unsatisfactory conversion of the alcohol, as well as the formation of large quantities of by-products when branched-chain alcohols are used.

It has been surprisingly found by the inventors that higher alcohol conversions and reduced by-product formation is achieved in the formation of enol ethers when the reaction between a branched-chain aldehyde and a branched-chain alcohol is performed in the temperature range of greater than about 125° C. and less than about 170° C. provided that the reaction mixture is at reflux at the reaction temperature. The reflux temperature of the reaction mixture may be controlled, for instance, by the addition of an appropriate solvent and/or the selection of an appropriate reaction pressure. This synthesis is particularly effective when branched-chain alcohols are used in the synthesis of enol ethers. It has additionally been found that these enol ethers may subsequently be reduced to saturated ethers under much milder reducing conditions than required in the reduction of acetals in prior art methods.

SUMMARY

In a first aspect, the present invention provides a process for preparing an enol ether said process comprising the steps of:
 i) contacting a branched-chain aldehyde with a branched-chain alcohol in the presence of a catalyst to form a reaction mixture, wherein the branched-chain aldehyde is branched at the beta position; and
 ii) heating the reaction mixture formed in step i) under reflux with continuous removal of water by-product, wherein the reaction temperature in step ii) is greater than about 125° C. and less than about 170° C.

In preferred embodiments, the alcohol has the formula (I):

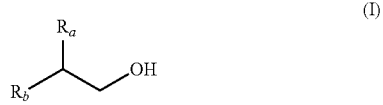

where $R_a$ and $R_b$ are independently selected from $C_1$ to $C_{18}$ alkyl, preferably $C_3$ to $C_{18}$ alkyl, more preferably $C_6$ to $C_{18}$ straight-chained alkyl.

In other preferred embodiments, the aldehyde has the formula (II):

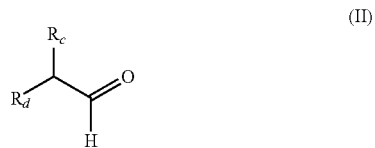

where $R_c$ and $R_d$ are independently selected from $C_1$ to $C_{18}$ alkyl, preferably $C_1$ to $C_{10}$ alkyl.

In additional embodiments, the process further comprises the step of:
iii) reducing the enol ether obtained from step ii) to form a saturated ether.

Also provided are processes which, following preparation of the ether compound, include formulation of a lubricating composition comprising the ether compound and use of the resulting lubricant composition for lubricating a surface, such as a surface of an internal combustion engine associated with an automotive vehicle.

DETAILED DESCRIPTION

The present invention provides a process for preparing an enol ether comprising the steps of:
i) contacting a branched-chain aldehyde with a branched-chain alcohol in the presence of a catalyst to form a reaction mixture; and
ii) heating the reaction mixture formed in step i) under reflux with continuous removal of water by-product, wherein the reaction temperature in step ii) is greater than about 125° C. and less than about 170° C.

This process is particularly advantageous as it has been found that the combination of performing the reaction in the temperature range of greater than about 125° C. and less than about 170° C. and performing the reaction under reflux conditions minimises the amount of by-products formed and increases the conversion of the starting materials during the synthesis of enol ethers from an aldehyde and an alcohol, particularly a branched-chain aldehyde and a branched-chain alcohol. The reflux temperature of the reaction mixture may be controlled by the addition of an appropriate solvent and/or the selection of an appropriate reaction pressure.

For the purposes of the present invention, the following terms as used herein shall, unless otherwise indicated, be understood to have the following meanings.

The term "enol ether" as used herein refers to an α,β-unsaturated alkenyl ether of the general formula $R_1R_2C\!=\!CR_3OR_4$ where $R_1$, $R_2$ and $R_4$ are independently selected from hydrocarbyl groups, $R_3$ is hydrogen and the double bond may have either E or Z configuration unless otherwise specified.

The term "branched-chain aldehyde" as used herein refers to a compound of the general formula: R—CHO, where R is a hydrocarbyl group comprising one branch at the beta-position relative to the carbonyl functional group (i.e. on the beta-carbon), optionally having additional branching elsewhere, and preferably having from 4 to 40 carbon atoms.

The term "branched-chain alcohol" as used herein refers to a compound with the general formula: R—OH, where R is a hydrocarbyl group, which is attached to the alcohol functional group (—OH) by a carbon atom, and wherein the hydrocarbyl group comprises at least one branch and preferably has from 4 to 40 carbon atoms. The alcohol may be a primary or a secondary alcohol, preferably a primary alcohol. The location of the at least one branch in the alcohol compound is not particularly limited, although it is preferred that the at least one branch is located at the beta-position relative to the alcohol functional group (i.e. on the beta-carbon).

The term "hydrocarbyl" as used herein, including as used in connection with the alcohol and aldehyde reactants employed in the process of the invention, refers to a group comprising a major proportion of hydrogen and carbon atoms, preferably consisting exclusively of hydrogen, carbon and oxygen atoms, more preferably consisting exclusively of hydrogen and carbon atoms, which group may be saturated or unsaturated, preferably saturated, and contains up to 40 carbon atoms. Examples of hydrocarbyl groups include hydrocarbyl groups containing from 4 to 36 carbon atoms, such as from 6 to 26 carbon atoms or from 8 to 24 carbon atoms.

Optionally, one or more of the carbon atoms, and any substituents attached thereto, of the hydrocarbyl group may be replaced with an oxygen atom (—O—). Where one or more of the carbon atoms, and any substituents attached thereto, of the hydrocarbyl group is replaced with —O—, from 2% to 35% of the carbon atoms are preferably replaced with —O—, or from 5% to 25%. In other examples, the hydrocarbyl group has 1 to 3 carbon atoms, and any substituents bonded thereto, replaced with —O—, for example 2 carbon atoms replaced with —O—. In other examples, none of the carbon atoms are replaced with —O—.

The hydrocarbyl group comprises at least one aliphatic portion which is acyclic, directly bonded to the alcohol (—OH) and aldehyde (—C(=O)H) functional groups of the branched-chain alcohol and the branched-chain aldehyde respectively, where the aliphatic, acyclic portion includes the branched-chain. The hydrocarbyl group may be entirely aliphatic or a combination of aliphatic and aromatic portions. In some examples, the hydrocarbyl group includes a branched aliphatic chain which is substituted by one or more aromatic groups.

Examples of hydrocarbyl groups therefore include acyclic groups, as well as groups that combine one or more acyclic portions (which can accommodate the requirement for branching in the alcohol and aldehyde) and one or more cyclic portions, which may be selected from carbocyclic, aryl and heterocyclyl groups. The hydrocarbyl group includes monovalent groups and polyvalent groups as specified and may, for example, include one or more groups selected from alkyl, alkenyl, alkynyl, carbocyclyl (e.g. cycloalkyl or cycloalkenyl), aryl and heterocyclyl.

The term "alkyl" as used herein refers to a monovalent straight- or branched-chain alkyl moiety containing from 1 to 40 carbon atoms. Examples of alkyl groups include alkyl groups containing from 1 to 30 carbon atoms, e.g. from 1 to 20 carbon atoms, e.g. from 1 to 18 carbon atoms. Particular examples include alkyl groups containing 4, 6, 8, 10, 12 or 14 carbon atoms. Unless specifically indicated otherwise, the term "alkyl" does not include optional substituents.

The term "cycloalkyl" as used herein refers to a monovalent saturated aliphatic hydrocarbyl moiety containing from 3 to 40 carbon atoms and containing at least one ring, wherein said ring has at least 3 ring carbon atoms. The cycloalkyl groups mentioned herein may optionally have alkyl groups attached thereto. Examples of cycloalkyl groups include cycloalkyl groups containing from 3 to 16 carbon atoms, e.g. from 3 to 10 carbon atoms. Particular examples include cycloalkyl groups containing 3, 4, 5 or 6 ring carbon atoms. Examples of cycloalkyl groups include groups that are monocyclic, polycyclic (e.g. bicyclic) or bridged ring system. Examples of cycloalkyl groups include cyclopropyl, cyclobutyl, cyclopentyl, cyclohexyl and the like. "Cycloalkenyl" groups correspond to non-aromatic cycloalkyl groups containing at least one carbon-carbon double bond.

The term "alkenyl" as used herein (and when not in connection with the unsaturation at the beta carbon of the alkenyl ether defined above) refers to a monovalent straight- or branched-chain alkyl group containing from 2 to 40 carbon atoms and containing, in addition, at least one carbon-carbon double bond, of either E or Z configuration unless specified. Examples of alkenyl groups include alkenyl groups containing from 2 to 28 carbon atoms, e.g. from 3 to 26 carbon atoms, e.g. from 4 to 24 carbon atoms. Examples of alkenyl groups include alkenyl groups containing from 2 to 20 carbon atoms, e.g. from 2 to 12 carbon atoms, e.g. from 2 to 10 carbon atoms. Particular examples include alkenyl groups containing 2, 3, 4, 5 or 6 carbon atoms. Examples of alkenyl groups include ethenyl, 2-propenyl, 1-butenyl, 2-butenyl, 3-butenyl, 1-pentenyl, 2-pentenyl, 3-pentenyl, 1-hexenyl, 2-hexenyl, 3-hexenyl and the like.

The term "alkylene" as used herein refers to a divalent straight- or branched-chain saturated hydrocarbyl group consisting of hydrogen and carbon atoms and containing from 1 to 30 carbon atoms. Examples of alkylene groups include alkylene groups that contain from 1 to 20 carbon atoms, e.g. from 1 to 12 carbon atoms, e.g. from 1 to 10 carbon atoms. Particular examples include alkylene groups that contain 1, 2, 3, 4, 5 or 6 carbon atoms.

The term "aryl" as used herein refers to an aromatic carbocyclic ring system containing from 6 to 14 ring carbon atoms. Examples of aryl groups include aryl groups containing from 6 to 10 ring carbon atoms, e.g. 6 ring carbon atoms. An example of an aryl group includes a group that is a monocyclic aromatic ring system or a polycyclic ring system containing two or more rings, at least one of which is aromatic. Examples of aryl groups include aryl groups that comprise from 1 to 6 exocyclic carbon atoms in addition to ring carbon atoms. Examples of aryl groups include aryl groups that are monovalent or polyvalent as appropriate. Examples of monovalent aryl groups include phenyl, benzyl naphthyl, fluorenyl, azulenyl, indenyl, anthryl and the like. An example of a divalent aryl group is 1,4-phenylene.

The term "heterocyclyl" as used herein refers to a saturated (e.g. heterocycloalkyl) or unsaturated (e.g. heteroaryl) heterocyclic ring moiety containing from 3 to 14 ring atoms, wherein said ring atoms include at least one ring carbon atom and at least one ring heteroatom selected from nitrogen, oxygen and sulphur. Examples of heterocyclyl groups include heterocyclyl groups that contain from 3 to 10 ring atoms, e.g. from 3 to 6 ring atoms. Particular examples include heterocyclyl groups that contain 5 or 6 ring atoms, including for example, groups that are saturated, unsaturated or aromatic. Examples of heterocyclyl groups include heterocyclyl groups that, in addition to ring carbon atoms, comprise from 1 to 6 exocyclic carbon atoms. Examples of heterocyclyl groups include those that are monovalent or polyvalent as appropriate.

The term "heteroaryl" as used herein refers to an aromatic heterocyclic ring system containing from 5 to 14 ring atoms, wherein said ring atoms include at least one ring carbon atoms and at least one ring heteroatom selected from nitrogen, oxygen and sulphur. Examples of heteroaryl groups include heteroaryl groups that are a monocyclic ring system or a polycyclic (e.g. bicyclic) ring system, containing two or more rings, at least one of which is aromatic. Examples of heteroaryl groups include those that, in addition to ring carbon atoms, comprise from 1 to 6 exocyclic carbon atoms. Examples of heteroaryl groups include those that are monovalent or polyvalent as appropriate. Examples of heteroaryl groups include furanyl, and benzo[b]furanyl groups.

The term "reaction temperature" as used herein refers to the temperature of the reaction mixture, for instance, inside the reactor or reaction vessel within which the reaction is performed. As will be appreciated by the skilled person, the reaction temperature may not always necessarily be the same as the temperature of the heating means applied to the reactor.

In some embodiments, the alcohol employed in the process of the invention has the formula (I):

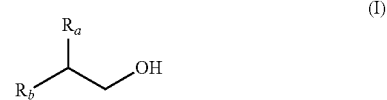

(I)

where $R_a$ and $R_b$ are independently selected from $C_1$ to $C_{18}$ alkyl, preferably $C_3$ to $C_{18}$ alkyl, more preferably $C_6$ to $C_{18}$ straight-chained alkyl. $R_a$ and $R_b$ may be branched-chain or preferably straight-chain. In some embodiments, $R_a$ and $R_b$ have different numbers of carbon atoms. For example, in some embodiments, $R_a$ and $R_b$ differ in carbon number by 1 to 3 carbon atoms. In preferred embodiments, the alcohol is 2-decyltetradecan-1-ol or 2-octyldodecan-1-ol.

The aldehyde is a branched-chain aldehyde having a single branch at the beta position (in relation to the carbonyl functional group) and optionally having additional branching elsewhere. As will be appreciated by the skilled person, aldehydes comprising two beta branches (i.e. tri-substitution at the beta position) cannot form an enol ether.

In some embodiments, the aldehyde employed in the process of the invention has the formula (II):

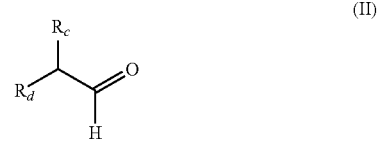

(II)

where $R_c$ and $R_d$ are independently selected from $C_1$ to $C_{18}$ alkyl, preferably $C_1$ to $C_{10}$ alkyl. $R_c$ and $R_d$ may be branched-chain or straight-chain. In some embodiments, $R_c$ and $R_d$ have different numbers of carbon atoms. In some embodiments, $R_c$ and $R_d$ differ in carbon number by 2 to 6 carbon atoms. For example, in some embodiments, $R_c$ has a total carbon number of $C_1$ to $C_3$ and $R_d$ has a total carbon number of $C_3$ to $C_6$ and $R_c$ and $R_d$ differ in carbon number by 2 to 4 carbon atoms.

In preferred embodiments, the aldehyde is 2-ethylhexanal, 2-methylbutanal, 2-methylpropanal, 2-ethylbutanal or 2-propylheptanal.

In some embodiments, the enol ether formed in the process of the invention has a total number of carbon atoms of from 20 to 60, preferably from 24 to 40, more preferably from 28 to 36 carbon atoms.

In some embodiments, the ether formed by the process of the invention has a total number of carbon atoms of from 20 to 60, preferably from 24 to 40, more preferably from 28 to 36 carbon atoms, and most preferably from 28 to 36 carbon atoms.

The process of the present invention may be utilized in order to prepare ether compounds from a wide range of commercially available aldehyde and alcohol feedstocks.

In some embodiments, the compounds are prepared from bio-derived feedstocks. For instance, the resulting ether compounds may contain greater than about 50%, such as greater than about 70%, or greater than about 80% by weight of biobased carbon. The biobased carbon content of the compounds may be measured according to ASTM D6866.

Enol Ether Synthesis

The molar ratio of alcohol to aldehyde used in accordance with the present invention is not particularly limited. In some embodiments, a molar excess of the aldehyde over the alcohol is used. This may minimise the quantity of acetal side product produced during the reaction. The aldehyde and alcohol are preferably contacted in a molar ratio of at least 1:1, preferably at least 2:1, more preferably at least 5:1.

The aldehyde and the alcohol reactants may be contacted by any suitable means of which the skilled person is familiar. For instance, the reactants may be contacted within a reactor and may be fed into the reactor either separately or premixed. Where a solid catalyst is employed as the catalyst, the reactants may initially all contact the solid catalyst at the same portion of the solid catalyst, or they may be added at different positions of the solid catalyst. The initial point of contact of the reactants with the solid catalyst is the point at which the reactants initially contact each other in the presence of the solid catalyst. The reactants may flow co-currently or counter-currently over the solid catalyst.

The process of the present invention may be carried out in any suitable heterogeneous or homogeneous catalytic reactor, in particular the known types of liquid-phase reactors (including but not limited to plug flow, continuously stirred tank, loop reactors or combinations thereof), provided that it is configured for continuous removal of water by-product. Reactive separations, such as catalytic distillation, can also be employed in accordance with the present invention, which may be useful in a continuous process where production and removal of products occurs simultaneously. Reactive distillation may also be used for the removal of water by-product in the process. The reactants may be in a gaseous phase and/or a liquid phase. The reaction can be carried out in a continuous, semi-continuous or a batch-type mode.

The aldehyde and alcohol reactants are contacted, typically in the liquid phase, and subsequently heated to a temperature which is suitable for achieving conversion of a major portion of the alcohol reactant to the corresponding enol ether and which avoids decomposition of the reactants and undesirable side reactions and does not, for instance, exceed the temperature limit at which any catalyst which is present remains stable. It has been found that a reaction temperature of greater than about 125° C. and less than about 170° C. represents a specific range over which surprising benefits, such as reduced by-product synthesis, have been found over and above that exhibited at different temperatures. It has been found by the inventors that at temperatures of below 125° C., acetal formation may become more prevalent whilst at temperatures above 170° C., it has been found that decomposition of the branched alcohols used in the process may occur. The problem of decomposition is not believed to be seen in the case of simple straight-chained alcohols employed in enol ether syntheses in the prior art. Both acetal formation and alcohol decomposition reduce the yield of the enol ether and increase the quantity of undesirable by-products which must subsequently be separated from the desired product. Thus, the range of temperatures employed in the present invention has been found to be particularly advantageous in combination with the other features of the invention, namely the use of a branched-chain aldehyde, a branched-chain alcohol, reflux conditions and an acidic catalyst. In preferred embodiments, the reactants are contacted at a temperature of from about 125° C. to about 165° C., more preferably about 130° C. to about 160° C., even more preferably about 140° C. to about 150° C.

In accordance with the present invention, the reaction of the alcohol and aldehyde is performed under reflux conditions. Thus, not only must the reaction temperature be kept within the above described range, the temperature must also be sufficient to achieve reflux of the reaction mixture. The term "reflux" as used herein refers to the common useage of the term, namely when the reaction mixture is at boiling point. Typically, at least some of the vapours produced during boiling are condensed and returned to the system from which they originated. By performing the reaction under reflux, it is possible to remove the water by-product during the reaction, driving the reaction to completion. As will be appreciated by the skilled person, the temperature and pressure required to achieve reflux for a specific reaction mixture will depend upon the aldehyde and the alcohol reactants used, as well as, for instance, the nature of any solvent that may be present. The skilled person would readily be able to tailor the reaction conditions so as to achieve reflux of the reaction mixture within the required temperature range. For example, the reflux temperature of the reaction mixture may be controlled by the addition of an appropriate solvent and/or the selection of an appropriate reaction pressure.

Therefore, the combination of performing the reaction between a branched-chain aldehyde and a branched-chain alcohol at a temperature of greater than about 125° C. and less than about 170° C. while the reaction is at reflux and with continuous removal of the water by-product results in significant benefits in the synthesis of enol ethers.

The reaction of the aldehyde and the alcohol may be performed over a range of pressures, provided that reflux conditions are maintained. In some embodiments, the reaction between the aldehyde and the alcohol is performed at atmospheric pressure, under reduced pressure or under greater than atmospheric pressure. A suitable range of pressures for use in connection with the present invention is about 10 to about 1,000 kPa. By contacting the reactants at atmospheric pressure, energy is not expended modifying the pressure in the reactor, making the reaction more energy efficient. Thus, in preferred embodiments, the reactants are contacted at atmospheric pressure. In the present application, atmospheric pressure is defined as 101.3 kPa. The pressure may be selected in order to ensure that the solvent boils within the temperature range about 125° C. to about 170° C., preferably about 125° C. to about 165° C., more preferably about 130° C. to about 160° C., even more preferably about 140° C. to about 150° C.

In accordance with the present invention, any of the temperature ranges mentioned above may be taken in combination with any of the pressure ranges described hereinbefore, provided that the reaction mixture may achieve reflux under the reaction conditions.

The reaction between the aldehyde and the alcohol in step ii) of the process may be performed under an inert atmosphere, such as under a nitrogen atmosphere.

Optionally, one or more solvents may be present in the reaction mixture. These solvents may be used to modify the boiling point of the reaction mixture, to form an azeotrope with water so as to facilitate distillation of water from the reaction mixture, to improve separation of water from the aldehyde or alcohol in the distillate, to dilute the reaction mixture, to provide reaction stability and/or to promote the reaction. Suitable solvents include xylenes, toluene, ethyl benzene, chlorobenzene, 2-ethyl-hexanal, 2-methyl-butanal, and mixtures thereof. The addition of a solvent in the reaction mixture may result in improved alcohol conversion, enol ether yield and may reduce by-product formation. These effects have been found by the inventors to be particularly evident when the solvent is xylenes and/or toluene, therefore preferably the solvent is xylenes and/or toluene, more preferably the solvent is toluene. In some embodiments, the aldehyde reactant may be used in molar excess and in further embodiments this excess aldehyde may be used as both solvent and reactant. The term xylenes' herein is used to refer to a single xylene isomer or mixtures of xylene isomers.

In the process of the present invention, the aldehyde and alcohol reactants are contacted in the presence of a catalyst. This catalyst may be used to facilitate and/or accelerate the reaction between the aldehyde and alcohol. The catalyst may be a homogeneous catalyst or a heterogeneous catalyst. In embodiments, the catalyst is an acidic catalyst, preferably a weak acid salt. The catalyst may be a solid acid catalyst. The weak acid salt may be formed in situ during step i) of the reaction process. Alternatively, the weak acid salt may be formed prior to being added to the reactants.

In embodiments, the catalyst may be a weak acidic salt comprising a pyridinium, collidinium or lutidinium cation and/or a p-toluenesulfonate anion. In alternative embodiments, the catalyst may be a weak acidic salt comprising a metal cation, such as an alkali metal or alkaline earth metal cation, and a hydrogensulfate anion. In embodiments, the weak acid salt is potassium hydrogensulfate or sodium hydrogensulfate. Preferably, the weak acidic salt is pyridinium p-toluenesulfonate.

In further embodiments, the catalyst may be selected from p-toluenesulfonic acid, sulfuric acid, potassium bisulfate, sodium bisulfate, potassium ($C_1$-$C_8$-alkyl)sulfonate, ($C_1$-$C_8$-alkyl)sulfonic acids, benzene sulfonic acid, methylsulfonic acid, N—($C_1$-$C_8$-alkyl)sulfamic acids, N,N-di($C_1$-$C_8$-alkyl) sulfamic acids, hydrochloric acid, phosphoric acid, ammonium nitrate, potassium bisulfate, cerium (III) chloride, iron (III) chloride, scandium(III) trifluoromethanesulfonimide, aluminium trifluoromethanesulfonate, bismuth trifluoromethanesulfonate, tetrabutylammonium tribromide, N-bromosuccinimide, N,N'-bis[3,5-bis(trifloro-methyl)phenyl]thiourea, an acidic ion-exchange resin, an aluminosilicate etherification catalyst or a zeolite.

Examples of suitable acidic ion-exchange resin catalysts include acidic macroreticular-type ion-exchange resins or an acidic gel-type ion-exchange resins. Typically, the acidic gel-type cation exchange resins that may be used are based on an insoluble cross-linked polymeric matrix, typically having a pore diameter of at most 30 Å. In preferred embodiments, the acidic gel-type cation exchange resins are based on a cross-linked polystyrene based matrix, preferably having a pore diameter of at most 30 Å. More preferably, the acidic gel-type cation exchange resins that may be used are based on a cross-linked polymeric matrix prepared by copolymerising styrene and divinyl benzene and preferably having a pore diameter of at most 30 Å.

In preferred embodiments, the acidic gel-type cation exchange resins are strong acid ion exchange resins, such as sulfonated resins. In particular, the acidic gel-type cation exchange resins are preferably based on a sulfonated insoluble cross-linked polymeric matrix preferably having a pore diameter of at most 30 Å. In a particularly preferred embodiment, the acidic gel-type cation exchange resin used is based on a sulfonated copolymer of styrene and divinyl benzene, preferably having a pore diameter of at most 30 Å.

Examples of suitable acidic gel-type cation exchange resins include, but are not limited to, the strong acid Dowex (trademark) gel-type ion exchange resins, the strong acid Amberlyst (trademark) gel-type ion exchange resins, the strong acid Diaion (trademark) gel-type ion exchange resins, the strong acid Lewatit (trademark) gel-type ion exchange resins, the strong acid Purolite (trademark) gel-type ion exchange resins, the strong acid gel-type ion exchange resins available from ResinTech Inc., and mixtures thereof.

The acidic macroreticular-type cation exchange resins useful in the present invention are typically based on an insoluble cross-linked polymeric matrix typically having a pore diameter in the range of from 50 to 1,000,000 Å. In preferred embodiments, the acidic macroreticular-type cation exchange resins used in the process of the present invention are based on a cross-linked polystyrene based matrix having a pore diameter in the range of from 50 to 1,000,000 Å. More preferably, the acidic macroreticular-type cation exchange resins useful in the process of the present invention are based on a cross-linked polymeric matrix prepared by copolymerising styrene and divinyl benzene, having a pore diameter in the range of from 50 to 1,000,000 Å.

In preferred embodiments, the acidic macroreticular-type cation exchange resins used in the process of the present invention are strong acid ion exchange resins, such as sulfonated resins. In particular, the acidic macroreticular-type cation exchange resins used in the process of the present invention are preferably based on a sulfonated insoluble cross-linked polymeric matrix preferably having a pore diameter in the range of from 50 to 1,000,000 Å. Thus, in a particularly preferred embodiment, the acidic macroreticular-type cation exchange resins used in the process of the present invention are sulfonated copolymers of styrene and divinyl benzene, having a pore diameter in the range of from 50 to 1,000,000 Å.

Suitable acidic macroreticular-type cation exchange resins include, but are not limited to, the strong acid Dowex macroreticular-type ion exchange resins, the strong acid Amberlyst macroreticular-type ion exchange resins, the strong acid Diaion macroreticular-type ion exchange resins, the strong acid Lewatit macroreticular-type ion exchange resins, the strong acid Purolite macroreticular-type ion exchange resins, the strong acid macroreticular-type ion exchange resins available from ResinTech Inc., and mixtures thereof.

Examples of suitable aluminosilicate etherification catalysts which may be used in accordance with the present invention include solid porous materials having acid sites or acid functionality. The aluminosilicate may thus optionally be treated or impregnated with an acid, such as phosphoric acid, phosphonic acid, sulfuric acid or a sulphonic acid. The aluminosilicate etherification catalyst used in accordance with the invention may be a microporous aluminosilicate or a mesoporous aluminosilicate.

In preferred embodiments, the aluminosilicate etherification catalyst is a zeolite. The zeolite may have at least one channel defined by a 10-membered or 12-membered ring.

The zeolite may be a large-pore zeolite having at least one channel having a diameter of at least 5 Å, at least 6 Å, or at least 7 Å.

In other embodiments, the zeolite has the framework type BEA, MFI, FAU or MOR, and therefore includes beta, pentasil, faujasite and mordenite zeolites. Examples of faujasites are zeolite Y and zeolite X.

The zeolite is preferably in the acidic (H) form. Thus, the zeolites include, for example, H-faujasites and H-mordenites, and the zeolite may be zeolite H—Y or zeolite H—X.

The density of acid sites in zeolites is dependent on the silica to alumina ratio (SAR) of the zeolite. The lower the SAR value the greater the proportion of aluminium atoms and the greater the density of acidic sites. Thus, for optimum etherification performance it is preferred to use zeolites having low SAR values. Thus, in some embodiments, the zeolite has an SAR of at most 100, for example in the range of from 1 to 100, in other embodiments has an SAR of at most 50, for example in the range of from 1 to 50, in further embodiments has an SAR of at most 20, for example in the range of from 1 to 20, in still further embodiments has an SAR of at most 15, for example in the range of from 1 to 15, and in yet further embodiments has an SAR of at most 10, for example in the range of from 1 to 10.

The above catalysts may be used alone or in combination with one or more other catalysts.

The quantity of catalyst used may be in the range of 0.002 to 3 wt %, preferably 0.002 to 1.5 wt %, more preferably 0.05 to 0.5 wt % of the combined weight of the reaction mixture, including solvent.

Where a bed of solid acid catalyst, such as an acidic ion-exchange resin, is employed in connection with the reaction in step ii), the flow rate of reactants, in terms of Liquid Hourly Space Velocity (LHSV) (volume of liquid feed stream/total volume of acetalization catalyst/hour), at which a pre-mixed aldehyde and alcohol reactant stream is contacted with the solid acid catalyst is suitably in the range of from 0.1 to 50 $h^{-1}$.

The beneficial effects such as increased enol ether yield and alcohol conversion and the reduction in by-product synthesis are particularly evident when a toluene or xylenes solvent is used in combination with the weak acid catalyst pyridinium p-toluenesulfonate, collidinium p-toluenesulfonate or lutidinium p-toluenesulfonate.

Following completion of the reaction in step ii), the enol ether may be isolated from the reaction mixture by known separation processes including filtration, chromatography (e.g. flash column chromatography) and/or distillation (e.g. vacuum distillation). A distillation column may be used to isolate the enol ether product following the reaction. The distillation may be performed in a conventional distillation column with a number of stages (e.g. ideal stages) commensurate with the reflux ratio required, for example between about 5 and about 50 ideal separation stages. Reactive separations such as catalytic distillation can be employed which may be useful in a continuous process where production and removal of products occurs simultaneously.

Where a homogeneous acid catalyst is used for catalysing the reaction between the aldehyde and the alcohol, a neutralization step may be included as part of isolating the enol ether compound, such as washing with alkaline, for example a saturated aqueous sodium bicarbonate, or by addition of a solid base such as potassium carbonate followed by agitation of the mixture, e.g. by stirring, and separation of the liquid from the solid by filtration.

During reaction between the aldehyde and alcohol, a water by-product is produced which is continuously removed. The continuous removal of water forces the equilibrium reaction to favour formation of the enol ether. By performing the reaction under reflux, this water by-product may be removed from the reaction mixture by separating the water from the reagents and/or solvent and/or product present in the condensed gases prior to returning them to the reaction mixture. Any form of reactor of which the person of skill in the art is familiar and which is capable of achieving that separation may be used. For instance, in some embodiments the reaction may be set up as a reactive distillation.

Any suitable reactive distillation column may be used provided it is configured for continuous water removal and has a number of stages (e.g. ideal stages) commensurate with the separation desired, for example between about 5 and about 50 ideal separation stages. The internal components of the distillation column may include, for example, sieve plates, unstructured and structured packing, bubble cap and mixtures thereof. For example, in the case of a reactive distillation column configured for by-product water removal, water vapour may be collected from a rectification section, without being returned to the reaction zone. Meanwhile, vaporized aldehyde and alcohol reactants may be re-condensed and returned to the reaction zone, for example a tray thereof, as liquid. Additionally, the enol ether product may be continuously withdrawn from the bottom of the stripping zone.

In embodiments where solvent is present in the reaction mixture, the solvent may be removed from the reaction mixture as part of continuous water by-product removal. This solvent may be separated from the water by-product and recycled to the reaction mixture. This may be performed by separation of the liquids if the solvent and water are immiscible, or by distillation to achieve separation by boiling point difference when, for instance, the solvent and water are partly miscible.

It has been surprisingly found that the particular combination of operating conditions according to the present invention maximises the alcohol conversion and enol ether yield in the reaction between the aldehyde and the alcohol and reduces by-product formation.

Prior art methods have been found to result in unsatisfactory conversion and in the formation of large quantities of by-products when branched-chain alcohols are used, as in the present invention. Comparative Examples 1 and 2 below, for instance, show that the conditions used in U.S. Pat. No. 5,053,556 are not effective at synthesising enol ethers when the alcohol in question is a branched alcohol such as 2-decyltetradecan-1-ol.

The benefits of the process of the present invention are particularly evident in branched alcohols with 4 to 40 carbon atoms, preferably 5 to 30 carbon atoms, more preferably 15 to 30 carbon atoms, most preferably 20 to 28 carbon atoms. These benefits are particularly evident in those branched-chain alcohols where the branch is in the beta position (in relation to the alcohol functional group). In particular, benefits are observed for branched alcohols of formula (I)

where the R groups are $C_1$ to $C_{18}$ alkyl, preferably $C_3$ to $C_{18}$ alkyl, more preferably $C_6$ to $C_{18}$ straight-chained alkyl.

The enol ethers produced from the reaction of these branched-chain alcohols with aldehydes are particularly suitable for use as lubricant base stocks when reduced to the corresponding ethers.

It has been found by the inventors that reactions where reflux of the reaction mixture is achieved within the range of greater than about 125° C. and less than about 170° C. results in an improved alcohol conversion and enol ether yield and reduces by-product synthesis. These by-products include acetal formation and the dehydrated alcohol. This is particularly evident for branched alcohols of formula (I), as described above.

The nature of the catalyst has also been found to impact the effectiveness of the synthesis of enol ethers from an aldehyde and a branched-chain alcohol. It has been found that the use of an acidic catalyst, in particular a weak acidic catalyst, is particularly beneficial as it results in improved alcohol conversion and enol ether yield and reduces by-product synthesis. It has further been found that pyridinium p-toluenesulfonate, collidinium p-toluenesulfonate or lutidinium p-toluenesulfonate are particularly suitable catalysts for this reaction.

In solution, pyridinium p-toluenesulfonate is in equilibrium with pyridine and p-toluenesulfonic acid. Pyridine is low boiling (115° C.) and is miscible with water, and therefore pyridine may be slowly lost during the reaction in the distilled water stream. This may be compensated for by the addition of fresh pyridine or by recovering the pyridine from the water stream and returning it to the reaction mixture. In contrast, higher boiling point bases such as collidine and lutidine may be used which avoid such losses.

Additionally, the inclusion of a solvent in the reaction mixture which is toluene or xylenes may further enhance alcohol conversion, enol ether yield and reduces by-product synthesis. These effects may be particularly evident when the toluene or xylene solvent is used in combination with the weak acid catalyst pyridinium p-toluenesulfonate, collidinium p-toluenesulfonate or lutidinium p-toluenesulfonate.

Reduction of the Enol Ether

The enol ether compound may be converted to the saturated ether by reduction, typically by catalytic hydrogenation in the presence of a hydrogenation catalyst, preferably a supported hydrogenation catalyst. An advantage of performing a hydrogenation with the enol ether is that a milder range of hydrogenation conditions may also be relied upon in comparison to the conditions required to reduce an acetal.

The hydrogenation reaction may be performed at any suitable pressures and temperatures at which the saturated ether is formed at an acceptable reaction rate, without risk of decomposition or substantial by-product formation that would otherwise negatively impact upon the advantages of the invention. Hydrogenation is, for example, suitably carried out at pressures of from atmospheric pressure to about 30,000 kPa absolute, preferably from about about 200 kPa absolute to about 3000 kPa absolute, more preferably from about 300 kPa absolute to about 1000 kPa absolute. Suitable temperatures at which the hydrogenation may be performed are, for example, from about 0° C. to about 350° C., preferably from about 50° C. to about 250° C., more preferably from about 80° C. to about 150° C. When operating under continuous conditions, the molar ratio of the enol ether to hydrogen can be from about 1:2 to about 1:100, and is preferably from about 1:4 to about 1:50. The reaction may be performed for any amount of time sufficient to reduce the enol ether, for example from about 0.1 to about 10 hours, preferably from about 1 to about 3 hours. When operating under batch conditions, the reactor may be charged to a pressure of from about 10 to about 1,000 kPa of hydrogen and the hydrogen pressure maintained at this pressure by adding hydrogen as the hydrogen is consumed during operation.

Where a bed of hydrogenation catalyst is employed in connection with the hydrogenation reaction, the flow rate of hydrogen-containing gas stream, in terms of Gas Hourly Space Velocity (GHSV) (volume of hydrogen-containing feed stream/total volume of hydrogenation catalyst/hour), at which enol ether reactant is contacted with hydrogen, or a mixture of hydrogen with inert gases, is suitably in the range of from about 50 to 10,000 $h^{-1}$.

Where a bed of hydrogenation catalyst is employed in connection with the hydrogenation reaction, the flow rate of an enol ether feed stream, in terms of Liquid Hourly Space Velocity (LHSV) (volume of feed stream/total volume of hydrogenation catalyst/hour), over the catalyst bed, is suitably in the range of from about 5 to about 1,000 $h^{-1}$, preferably from about 10 to about 500 $h^{-1}$, more preferably from about 20 to about 200 $h^{-1}$, most preferably from about 25 to about 100 $h^{-1}$.

In some embodiments, the hydrogenation catalyst used in the hydrogenation reaction comprises a metal selected from nickel, palladium, platinum, rhodium, ruthenium, cobalt, copper and combinations thereof. Preferably, the catalyst comprises palladium or nickel. The catalyst may be supported with a support material selected from carbon, silica, alumina, silica-alumina, and aluminosilicate, preferably carbon. The carbon, where used, can be any one of the many forms of carbon e.g. graphite or activated carbon.

The catalytic metal may be deposited or impregnated on the support using conventional mixing or precipitation techniques. The catalyst composition suitably has a catalytic metal content of about 0.05% w/w to about 80% w/w. Within this range, when a relatively less active metal, such as nickel, is used as the catalytic metal, it is suitably used towards the higher end of this range, whereas when a relatively more active metal such as palladium is used as the catalytic metal, it is preferably used at the lower end of this range. The skilled person is able to select a suitable metal loading depending on the particular catalytic metal used. Thus, for instance, the preferred range for the less active catalytic metals is suitably from about 20% w/w to about 80% w/w, whereas for the more active catalytic metals, such as palladium, the preferred range is from about 0.05% w/w to about 20% w/w. These weight ranges are based solely on the weight of the catalytic metal and the support and does not take into account any water or moisture content associated with either component.

The hydrogenation reaction may optionally be carried out in the presence of a solvent. Examples of such solvents include aprotic, hydrocarbon solvents such as pentane, heptane and/or toluene. A sufficient amount of solvent can be used to dilute the enol ether reactant to the desired concentration to facilitate handling and/or to maintain the reaction mass in solution.

The hydrogenation of the enol ether with hydrogen in the presence of a catalyst composition as described above can be carried out in a slurry reactor, a fixed bed reactor, a spouted bed reactor or any other suitable reactor configuration such as, for example, a moving bed reactor. The enol ether reactant may be in a gaseous phase and/or a liquid phase. The reaction can be carried out in a continuous, semi-continuous or a batch-type mode. The average residence time of the enol ether reactant in contact with the catalyst composition during the formation of the corresponding saturated ether compound is suitably from about 5 minutes to about 30 hours, preferably from about 15 minutes to about 10 hours. As the skilled person is aware, a convenient way of modifying the residence time of the reactant in the hydrogenation reaction is, for instance, to adjust the flow rate of an enol ether reactant stream over a bed of the hydrogenation catalyst, as described hereinbefore. The LHSV rate adopted may be used to determine the residence time of the reactant in the hydrogenation reaction. LHSV may be considered to be the inverse of residence time and therefore residence time may be calculated as the reciprocal of LHSV (where LHSV has the unit $h^{-1}$). For example, an LHSV of $2\ h^{-1}$ is equal to a residence time of 30 minutes.

The desired ether product may be isolated from the reaction mixture, by known separation processes including filtration, chromatography (e.g. flash column chromatography) and/or distillation (e.g. vacuum distillation), filtration and distillation being favoured on an industrial scale.

A particular advantage of synthesising ethers from enol ethers as opposed to acetals is the milder reduction conditions required by the process. The reduction of acetals is typically performed at pressures of from about 1,500 kPa absolute to about 30,000 kPa absolute and at temperatures of from about 100° C. to about 350° C. This makes the process more costly and energy inefficient.

Another advantage of the present invention is that during the synthesis of ethers from acetals an alcohol by-product is formed. Therefore, a further purification step is necessary in order to obtain the ether product. The synthesis of ethers from enol ethers according to the present invention does not necessarily result in any by-product formation, improving the atomic efficiency and removing the requirement for purification from undesirable by-products.

Lubricant Composition/Formation

Particularly Preferred Ether End Products that May be Prepared by Means of the Present invention include ether base stocks for lubricant compositions. In some embodiments, the process of the present invention may further include the step of blending the ether product obtained from the process into a lubricant composition.

The process of the present invention therefore represents a means of preparing an ether which is useful as a lubricating base stock which avoids the formation of corrosive intermediates and which may be isolated from the reaction mixture more readily. By operating the process for the reaction of an aldehyde and an alcohol in accordance with the present invention, it is possible to provide good conversion of the aldehyde to the enol ether and ether products, and with high selectivity.

The ether compounds described herein may be used to improve the dispersancy properties (for example, by improving soot and sludge dispersancy) and/or viscosity profile (for example, by decreasing deposit forming tendency and/or reducing oxidatively induced thickening) of a lubricant composition, such as a lubricant composition for an internal combustion engine, preferably associated with an automotive vehicle.

In accordance with another embodiment, the process of the invention also further comprises blending the ether obtained from the process into a lubricant composition by blending the ether with one or more additional base stocks and/or one or more lubricant additives. The ether obtained from the process of the invention may be miscible with conventional base stocks, including hydrocarbon base stocks, as well as with conventional lubricant additives. Moreover, such ether compounds may be used in a lubricant composition in a relatively high amount (for example, in an amount of greater than about 1% by weight, such as greater than about 5% by weight, greater than about 10% by weight, greater than about 20% by weight or greater than about 30% by weight). These lubricant compositions may comprise these weight percentages of ether whilst meeting elastomer compatibility requirements for lubricant compositions Base stocks other than the ether compound formed in the process of the present invention which are suitable for use blending for preparing a lubricant composition include non-aqueous base stocks, such as Group I, Group II, Group III, Group IV and Group V base stocks.

The lubricant composition may comprise a single lubricant additive, though it will typically comprise a combination of lubricant additives. The lubricant additives will typically be present in the lubricant composition in an amount of from about 5% to about 40% by weight, such as about 10% to about 30% by weight.

Suitable lubricant additives include detergents (including metallic and non-metallic detergents), friction modifiers, dispersants (including metallic and non-metallic dispersants), viscosity modifiers, dispersant viscosity modifiers, viscosity index improvers, pour point depressants, anti-wear additives, rust inhibitors, corrosion inhibitors, antioxidants (sometimes also called oxidation inhibitors), anti-foams (sometimes also called anti-foaming agents), seal swell agents (sometimes also called seal compatibility agents), extreme pressure additives (including metallic, non-metallic, phosphorus containing, non-phosphorus containing, sulphur containing and non-sulphur containing extreme pressure additives), surfactants, demulsifiers, anti-seizure agents, wax modifiers, lubricity agents, anti-staining agents, chromophoric agents, metal deactivators, and mixtures of two or more thereof.

In some embodiments, the lubricant composition comprises a detergent. Examples of detergents include ashless detergents (that is, non-metal containing detergents) and metal-containing detergents. Suitable non-metallic detergents are described for example in U.S. Pat. No. 7,622,431. Metal-containing detergents comprise at least one metal salt of at least one organic acid, which is called soap or surfactant. Suitable organic acids include for example, sulphonic acids, phenols (suitably sulphurised and including for example, phenols with more than one hydroxyl group, phenols with fused aromatic rings, phenols which have been modified for example, alkylene bridged phenols, and Mannich base-condensed phenols and saligenin-type phenols, produced for example by reaction of phenol and an aldehyde under basic conditions) and sulphurised derivatives thereof, and carboxylic acids including for example, aromatic carboxylic acids (for example hydrocarbyl-substituted salicylic acids and derivatives thereof, for example hydrocarbyl substituted salicylic acids and sulphurised derivatives thereof).

In some embodiments, the lubricant composition comprises a friction modifier. Suitable friction modifiers include for example, ash-producing additives and ashless additives. Examples of suitable friction modifiers include fatty acid derivatives including for example, fatty acid esters, amides, amines, and ethoxylated amines. Examples of suitable ester friction modifiers include esters of glycerol for example, mono-, di-, and tri-oleates, mono-palmitates and mono-myristates. A particularly suitable fatty acid ester friction modifier is glycerol monooleate. Examples of suitable friction modifiers also include molybdenum compounds for example, organo molybdenum compounds, molybdenum dialkyldithiocarbamates, molybdenum dialkylthiophosphates, molybdenum disulphide, tri-molybdenum cluster dialkyldithiocarbamates, non-sulphur molybdenum compounds and the like. Suitable molybdenum-containing compounds are described for example, in EP 1533362 A1 for example in paragraphs [0101] to [0117].

In some embodiments, the lubricant composition comprises a dispersant. Examples of suitable ashless dispersants include oil soluble salts, esters, amino-esters, amides, imides and oxazolines of long chain hydrocarbon-substituted mono- and polycarboxylic acids or anhydrides thereof; thiocarboxylate derivatives of long chain hydrocarbons; long chain aliphatic hydrocarbons containing polyamine moieties attached directly thereto; Mannich condensation products formed by condensing a long chain substituted phenol with formaldehyde and polyalkylene polyamine; Koch reaction products and the like.

In some embodiments, the lubricant composition comprises a dispersant viscosity modifier. Examples of suitable dispersant viscosity modifiers and methods of making them are described in WO 1999/021902, WO 2003/099890 and WO 2006/099250.

In some embodiments, the lubricant composition comprises a viscosity index improver. Examples of suitable viscosity modifiers include high molecular weight hydrocarbon polymers (for example polyisobutylene, copolymers of ethylene and propylene and higher alpha-olefins); polyesters (for example polymethacrylates); hydrogenated poly (styrene-co-butadiene or isoprene) polymers and modifications (for example star polymers); and esterified poly (styrene-co-maleic anhydride) polymers. Oil-soluble viscosity modifying polymers generally exhibit number average molecular weights of at least about 15000 to about 1000000, such as about 20000 to about 600000 as determined by gel permeation chromatography or light scattering methods.

In some embodiments, the lubricant composition comprises a pour point depressant. Examples of suitable pour point depressants include $C_8$ to $C_{18}$ dialkyl fumarate/vinyl acetate copolymers, methacrylates, polyacrylates, polyarylamides, polymethacrylates, polyalkyl methacrylates, vinyl fumarates, styrene esters, condensation products of haloparaffin waxes and aromatic compounds, vinyl carboxylate polymers, terpolymers of dialkyfumarates, vinyl esters of fatty acids and allyl vinyl ethers, wax naphthalene and the like. In at least some examples, the at least one lubricant additive includes at least one anti-wear additive. Examples of suitable anti-wear additives include non-phosphorus containing additives for example, sulphurised olefins. Examples of suitable anti-wear additives also include phosphorus-containing anti-wear additives. Examples of suitable ashless phosphorus-containing anti-wear additives include trilauryl phosphite and triphenylphosphorothionate and those disclosed in paragraph [0036] of US 2005/0198894. Examples of suitable ash-forming, phosphorus-containing anti-wear additives include dihydrocarbyl dithiophosphate metal salts. Examples of suitable metals of the dihydrocarbyl dithiophosphate metal salts include alkali and alkaline earth metals, aluminium, lead, tin, molybdenum, manganese, nickel, copper and zinc. Particularly suitable dihydrocarbyl dithiophosphate metal salts are zinc dihydrocarbyl dithiophosphates (ZDDP).

In some embodiments, the lubricant composition comprises a rust inhibitor. Examples of suitable rust inhibitors include non-ionic polyoxyalkylene polyols and esters thereof, polyoxyalkylene phenols, polyoxyalkylene polyols, anionic alky sulphonic acids, zinc dithiophosphates, metal phenolates, basic metal sulphonates, fatty acids and amines.

In some embodiments, the lubricant composition comprises a corrosion inhibitor. Examples of suitable corrosion inhibitors include phosphosulphurised hydrocarbons and the products obtained by the reaction of phosphosulphurised hydrocarbon with an alkaline earth metal oxide or hydroxide, non-ionic polyoxyalkylene polyols and esters thereof, polyoxyalkylene phenols, thiadiazoles, triazoles and anionic alkyl sulphonic acids. Examples of suitable epoxidised ester corrosion inhibitors are described in US 2006/0090393.

In some embodiments, the lubricant composition comprises an antioxidant. Examples of suitable antioxidants include alkylated diphenylamines, N-alkylated phenylenediamines, phenyl-a-naphthylamine, alkylated phenyl-a-naphthylamines, dimethylquinolines, trimethyldihydroquinolines and oligomeric compositions derived therefrom, hindered phenolics (including ashless (metal-free) phenolic compounds and neutral and basic metal salts of certain phenolic compounds), aromatic amines (including alkylated and non-alkylated aromatic amines), sulphurised alkyl phenols and alkali and alkaline earth metal salts thereof, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds (for example, copper dihydrocarbyl thio- or thio-phosphate, copper salts of a synthetic or natural carboxylic acids, for example a $C_8$ to $C_{18}$ fatty acid, an unsaturated acid or a branched carboxylic acid, for example basic, neutral or acidic Cu(I) and/or Cu(II) salts derived from alkenyl succinic acids or anhydrides), alkaline earth metal salts of alkylphenolthioesters, suitably containing $C_5$ to $C_{12}$ alkyl side chains, calcium nonylphenol sulphide, barium t-octylphenyl sulphide, dioctylphenylamine, phosphosulphised or sulphurised hydrocarbons, oil soluble phenates, oil soluble sulphurised phenates, calcium dodecylphenol sulphide, phosphosulphurised hydrocarbons, sulphurised hydrocarbons, phosphorus esters, low sulphur peroxide decomposers and the like.

In some embodiments, the lubricant composition comprises an antifoam agent. Examples of suitable anti-foam agents include silicones, organic polymers, siloxanes (including poly siloxanes and (poly) dimethyl siloxanes, phenyl methyl siloxanes), acrylates and the like.

In some embodiments, the lubricant composition comprises a seal swell agent. Examples of suitable seal swell agents include long chain organic acids, organic phosphates, aromatic esters, aromatic hydrocarbons, esters, (for example butylbenzyl phthalate) and polybutenyl succinic anhydride.

The lubricant composition may comprise lubricant additives in the amounts shown in Table 1.

TABLE 1

| | Lubricant composition | |
|---|---|---|
| Additive type | Suitable amount (actives) if present by weight | Preferred amount (actives) if present by weight |
| Phosphorus-containing anti-wear additives | Corresponding to about 10 to about 6000 ppm P | Corresponding to about 10 to about 1000 ppm P |

TABLE 1-continued

| | Lubricant composition | |
|---|---|---|
| Additive type | Suitable amount (actives) if present by weight | Preferred amount (actives) if present by weight |
| Molybdenum-containing anti-wear additives | Corresponding to about 10 to about 1000 ppm Mo | Corresponding to about 40 to about 600 ppm Mo |
| Boron-containing anti-wear additives | Corresponding to about 10 to about 500 ppm B | Corresponding to about 50 to about 100 ppm B |
| Friction modifiers | About 0.01 to about 5% | About 0.01 to about 1.5% |
| Molybdenum-containing friction modifiers | Corresponding to about 10 to about 1000 ppm Mo | Corresponding to about 400 to about 850 ppm Mo |
| Dispersants | About 0.1 to about 20% | About 0.1 to about 8% |
| Detergents | About 0.01 to about 6% | About 0.01 to about 4% |
| Viscosity index improvers | About 0.01 to about 20% | About 0.01 to about 15% |
| Pour point depressants | About 0.01 to about 5% | About 0.01 to about 1.5% |
| Corrosion and/or rust inhibitors | About 0.01 to about 5% | About 0.01 to about 1.5% |
| Anti-oxidants | About 0.01 to about 10% | About 0.5 to 5 about % |
| Antifoams containing silicon | Corresponding to about 1 to about 20 ppm Si | Corresponding to about 1 to about 10 ppm Si |

The lubricant compositions preparable in accordance with the present invention may have a kinematic viscosity at 40° C. of less than about 60 cSt, such as less than about 55 cSt, or less than about 50 cSt. The lubricant compositions may have a kinematic viscosity at 100° C. of less than about 12 cSt, such as less than about 10 cSt, or less than about 9.5 cSt. The lubricant compositions may have a viscosity index of greater than about 100, such as greater than about 110, or greater than about 120. The kinematic viscosity at 40° C. and the kinematic viscosity at 100° C. may be measured according to ASTM D445. The viscosity index may be calculated according to ASTM D2270.

The lubricant compositions may have a Noack volatility of less than about 25%, such as less than about 15%, or less than about 10% by weight. Noack volatility may be measured according to CEC-L-40-A-93.

The lubricant compositions may have a viscosity at 150° C. and a shear rate of $10^6$ s$^{-1}$ of no greater than 3 cP, such as no greater than 2.8 cP. This high temperature high shear viscosity may be measured according to CEC-L-36-A-90.

The lubricant compositions may have at least one of:
an oxidative stability performance on a CEC-L-088-02 and/or CEC L-111-16 test indicated by an absolute viscosity increase at 40° C. of no more than 45 cSt, such as no more than 35 cSt or no more than 25 cSt; a fuel economy performance on a CEC-L-054-96 test of at least 2.5%, such as at least 3%; and a piston cleanliness performance on a CEC-L-088-02 and/or CEC L-111-16 test indicated by an overall piston merit of at least 8.5, such as 9.

The lubricant compositions may have a cold-crankcase simulator performance at −30° C. of less than about 3000, such as less than about 2800, or less than about 2750, for example as measured according to ASTM D5293.

Preferred lubricant compositions meet the requirements set out in SAE J300.

In a yet further embodiment of the invention, after the lubricant composition has been prepared, the process may further comprise lubricating a surface with the lubricant composition by supplying the lubricant composition to a surface for lubrication.

Suitable surfaces include those in power transmission systems for example drive lines and gear boxes for example for vehicles including for example passenger vehicles and heavy duty vehicles; and those in internal combustion engines, for example the crankcases of internal combustion engines. Suitable surfaces also include those in turbine bearings for example in water turbine bearings.

Suitable internal combustion engines include, for example, engines used in automotive applications, engines used in marine applications and engines used in land-based power generation plants. The lubricant compositions are particularly suited to use in an automotive internal combustion engine.

The invention will now be described with reference to the accompanying examples, which are not limiting in nature.

EXAMPLES

Comparative Example 1—Synthesis of (Z)-1-((2-ethylhex-1-en-1-yl)oxy)decane

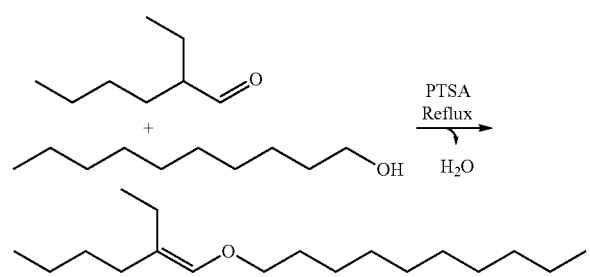

To a 3-necked round bottom flask equipped with a Dean-Stark receiver and a thermometer was added lauryl alcohol (30 g, 0.16 mmol), 2-ethylhexanal (30 g, 0.23 mmol) and p-toluenesulfonic acid (PTSA) (0.6 g, 2 mol %). The reaction mixture was heated to 200° C. and under reflux with stirring for 4 hours and the water continuously removed. GC analysis after removal of the volatiles showed 3% alcohol remaining after 4 hours and ~95% of the (Z)-1-((2-ethylhex-1-en-1-yl)oxy)decane (RMM=296) with a small amount of ester formation.

This reaction was performed using the same reagents and under those conditions used in U.S. Pat. No. 5,053,556 (Example 3 thereof), with substantially the same result.

Comparative Example 2—Synthesis of (Z)-11-(((2-ethylhex-1-en-1-yl)oxy)methyl)tricosane using 2-decyltetradecan-1-ol

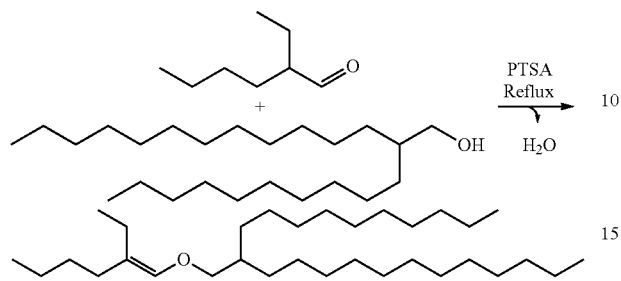

To a 3-necked round bottom flask equipped with a Dean-Stark receiver and a thermometer was added 2-decyltetradecan-1-ol (93 g, 0.26 mmol), 2-ethylhexanal (49 g, 0.38 mmol) and p-toluenesulfonic acid (1 g, 2 mol %). The reaction mixture was heated to 200° C. and under reflux with stirring for 4 hours and the water continuously removed. GC analysis after removal of the volatiles gave a mixture comprised of 26% alcohol, 5% dehydrated alcohol (11-methylenetricosane+isomers), 63% of the (Z)-11-(((2-ethylhex-1-en-1-yl)oxy)methyl)tricosane and 7% acetal.

This reaction was performed using a branched alcohol under those conditions used in U.S. Pat. No. 5,053,556 (Example 3 thereof) and in the above Comparative Example 1. This shows that, under these conditions and with a branched-chain alcohol, there is unsatisfactory alcohol conversion and significant quantities of the dehydrated alcohol and acetal by-products are formed.

Example 3—Synthesis of (Z)-11-(((2-ethylhex-1-en-1-yl)oxy)methyl)tricosane

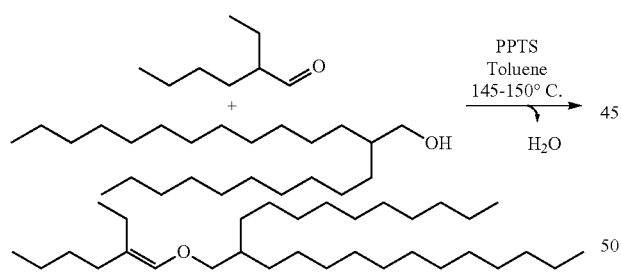

To a 3-necked round bottom flask equipped with a Dean-Stark receiver and a thermometer was added 2-decyltetradecan-1-ol (25 g, 71 mmol), toluene (15 g), 2-ethylhexanal (25 g, 194 mmol, 3 equiv.) and pyridinium p-toluenesulfonate (PPTS) (68 mg, 0.27 mmol, 0.4 mol %). The reaction mixture was heated in an oil bath to a temperature of 145-150° C. resulting in vigorous reflux. The reaction progress was monitored by GC and after ca. 5 hr complete conversion of the alcohol was observed. The reaction was cooled to room temperature overnight under an $N_2$ atmosphere before $K_2CO_3$ (150 mg) was added and the mixture filtered. The volatiles were removed to give the (Z)-11-(((2-ethylhex-1-en-1-yl)oxy)methyl)tricosane product as a yellow oil (<5% alcohol was observed by GC). This example demonstrates that the process of the invention results in good alcohol conversion and substantially no by-product formation. When compared to Comparative Example 2, which uses the same starting materials but under different conditions, the benefit of the reaction conditions used in the process of the invention are clear.

Example 4—3× Scale-Up Synthesis of (Z)-11-(((2-ethylhex-1-en-1-yl)oxy)methyl)tricosane

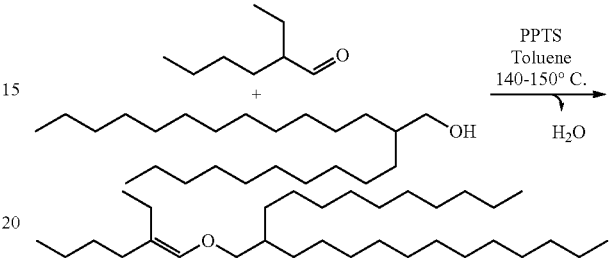

To a 3-necked round bottom flask equipped with a Dean-Stark receiver and a thermometer was added 2-decyltetradecan-1-ol (75 g, 211 mmol), toluene (25 g), 2-ethylhexanal (41 g, 320 mmol, 1.5 equiv.) and pyridinium p-toluenesulfonate (200 mg, 0.80 mmol, 0.4 mol %). The reaction mixture was heated in an oil bath to a temperature of 145-150° C. resulting in vigorous reflux. The reaction progress was monitored by GC and after ca. 6 hr complete the reaction was cooled to room temperature overnight under an $N_2$ atmosphere before $K_2CO_3$ (220 mg) was added and the mixture filtered. The volatiles were removed to give the (Z)-11-(((2-ethylhex-1-en-1-yl)oxy)methyl)tricosane product as a yellow oil (<10% alcohol was observed by GC).

This example demonstrates that the reaction is capable of being scaled up without significant changes in conversion or product purity.

Example 5—Synthesis of (Z)-11-(((2-ethylhex-1-en-1-yl)oxy)methyl)tricosane Using PTSA

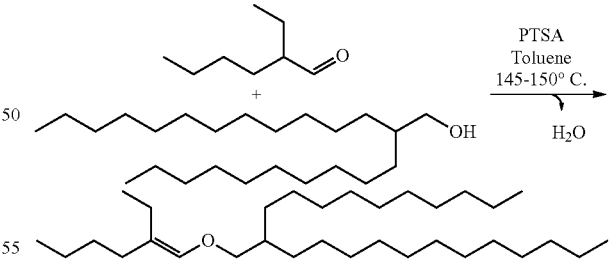

To a 3-necked round bottom flask equipped with a Dean-Stark receiver and a thermometer was added 2-decyltetradecan-1-ol (62 g, 0.18 mmol), 2-ethylhexanal (57 g, 0.44 mmol), toluene (36 g) and p-toluenesulfonic acid (0.16 g, 0.5 mol %). The reaction mixture was heated in an oil bath to a temperature of 145-150° C. with continuous removal of water. After ca. 5 hr the mixture was cooled to rt overnight under an $N_2$ before $K_2CO_3$ (220 mg) was added and the mixture filtered. The volatiles were removed to give a mixture comprised of 95% of the (Z)-11-(((2-ethylhex-1-en- 1-yl)oxy)methyl)tricosane, 4% alcohol and 1% dehydrated alcohol (11-methylenetricosane+isomers) as a yellow oil.

This example highlights that PTSA may be used as a catalyst without significant changes in alcohol conversion and by-product formation when compared to Examples 3 and 4.

Example 6—Synthesis of (Z)-11-(((2-ethylhex-1-en-1-yl)oxy)methyl)tricosane Using PTSA and Pyridine

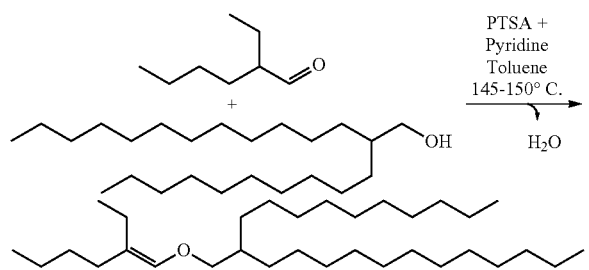

To a 3-necked round bottom flask equipped with a Dean-Stark receiver and a thermometer was added 2-decyltetradecan-1-ol (62 g, 0.18 mmol), 2-ethylhexanal (57 g, 0.44 mmol), toluene (36 g), p-toluenesulfonic acid (0.16 g, 0.5 mol %), and pyridine (71 µL, 0.5 mol %). The reaction mixture was heated in an oil bath to a temperature of 145-150° C. with continuous removal of water. After ca. 5 hr the mixture was cooled to rt overnight under an $N_2$ before $K_2CO_3$ (220 mg) was added and the mixture filtered. The volatiles were removed to give a mixture comprised of 98% of the (Z)-11-(((2-ethylhex-1-en-1-yl)oxy)methyl)tricosane, <1% alcohol and <1% dehydrated alcohol (11-methylenetricosane+isomers) as a colourless oil.

This example demonstrates that the PPTS catalyst may be formed in situ from PTSA and pyridine without significant changes in alcohol conversion and by-product formation when compared to Examples 3 to 5.

Example 7—Synthesis of (Z)-11-(((2-ethylhex-1-en-1-yl)oxy)methyl)tricosane with PTSA and Collidine

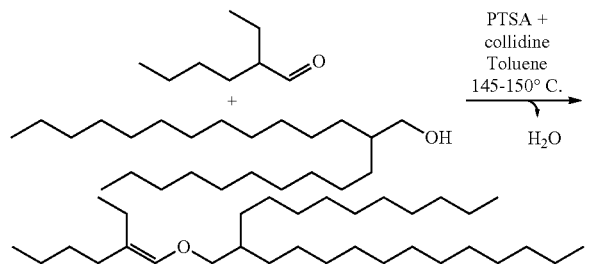

To a 3-necked round bottom flask equipped with a Dean-Stark receiver and a thermometer was added 2-decyltetradecan-1-ol (60 g, 0.17 mmol), 2-ethylhexanal (60 g, 0.46 mmol), toluene (36 g), p-toluenesulfonic acid (0.16 g, 0.5 mol %), and 2,4,6-trimethyl pyridine (0.11 mL, 0.5 mol %). The reaction mixture was heated in an oil bath to a temperature of 145-150° C. with continuous removal of water. After ca. 5 hr the mixture was cooled to rt overnight under an $N_2$ atmosphere. Analysis by GC gave a mixture comprised of 81% of the (Z)-11-(((2-ethylhex-1-en-1-yl)oxy)methyl)tricosane, 7.5% alcohol, 11% acetal and <1% dehydrated alcohol (11-methylenetricosane+isomers).

This example demonstrates that the catalyst formed in situ from PTSA and collidine may be used in the synthesis according to the present invention.

Example 8—Synthesis of (Z)-11-(((2-ethylhex-1-en-1-yl)oxy)methyl)tricosane with PTSA and 2,6-lutidine

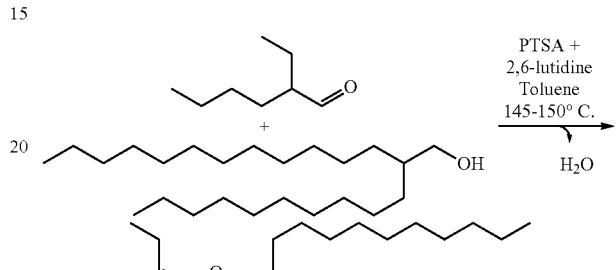

To a 3-necked round bottom flask equipped with a Dean-Stark receiver and a thermometer was added 2-decyltetradecan-1-ol (62 g, 0.17 mmol), 2-ethylhexanal (60 g, 0.46 mmol), toluene (36 g), p-toluenesulfonic acid (0.16 g, 0.5 mol %), and 2,6-dimethyl pyridine (0.1 mL, 0.5 mol %). The reaction mixture was heated in an oil bath to a temperature of 145-150° C. with continuous removal of water. After ca. 5 hr the mixture was cooled to rt overnight under an $N_2$ atmosphere before $K_2CO_3$ (1 g) was added and the volatiles removed to give a mixture comprised of 82% of the (Z)-11-(((2-ethylhex-1-en-1-yl)oxy)methyl)tricosane, <1% alcohol, <1% dehydrated alcohol (11-methylenetricosane+isomers) and 17% acetal as a yellow oil.

This example demonstrates that the catalyst formed in situ from PTSA and 2,6-lutidine may be used in the synthesis according to the present invention.

Example 9—Synthesis of (Z)-11-(((2-ethylhex-1-en-1-yl)oxy)methyl)tricosane at 300 mbar

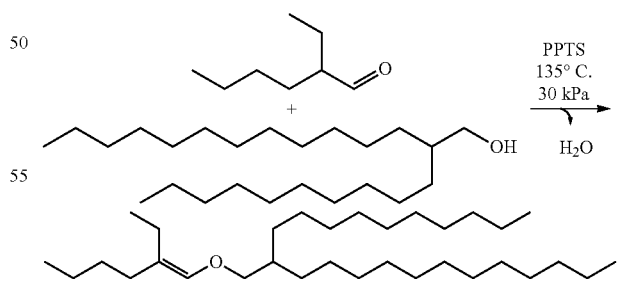

To a 3-necked round bottom flask equipped with a Dean-Stark receiver and a thermometer was added 2-decyltetradecan-1-ol (93 g, 0.26 mol), 2-ethylhexanal (101 g, 0.78 mol) and pyridinium p-toluenesulfonate (0.3 g, 0.5 mol %). The reaction mixture was heated to 135° C. at 30 kPa with stirring for 6 hours and the water continuously removed. GC analysis after removal of the volatiles and quench with K₂CO₃ gave a mixture comprised of 0.5% alcohol, 0.5% dehydrated alcohol (11-methylenetricosane+isomers), 92% of the (Z)-11-(((2-ethylhex-1-en-1-yl)oxy)methyl)tricosane and 4% acetal.

This Example demonstrates that the reaction may be performed at reduced pressure and therefore at reduced temperature, although still within the specified temperature range according to the invention and still adequate to achieve reflux. Additionally, this example demonstrates that no additional solvent is necessary in the reaction and that the aldehyde reagent can be used as both a reactant and solvent for the reaction.

Comparative Example 10—Synthesis of (Z)-11-(((2-ethylhex-1-en-1-yl)oxy)methyl)tricosane in an Uncatalyzed Control Reaction

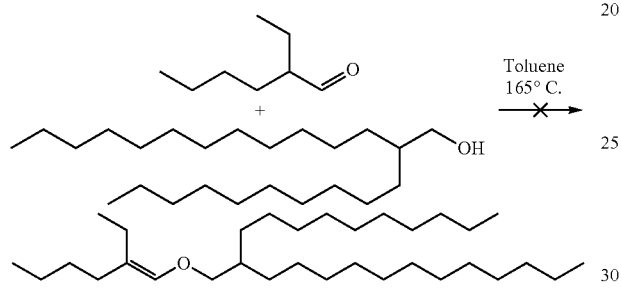

To a 3-necked round bottom flask equipped with a Dean-Stark receiver and a thermometer was added 2-decyltetradecan-1-ol (50 g, 0.14 mmol), 2-ethylhexanal (50 g, 0.39 mol), and toluene (30 g). The reaction mixture was heated in an oil bath at 165° C. with continuous removal of water. After ca. 6 hr the mixture was cooled to rt overnight under N₂ before K₂CO₃ (220 mg) was added and the mixture filtered. The volatiles were removed to give less than 5% conversion to the (Z)-11-(((2-ethylhex-1-en-1-yl)oxy) methyl)tricosane by GC analysis.

This example demonstrates that the addition of solvent alone, without the addition of a catalyst, does not result in the desired reaction.

Comparative Example 11—Synthesis of (Z)-11-(((2-ethylhex-1-en-1-yl)oxy)methyl)tricosane Using 2-ethylhexanal Dimethyl Acetal as Starting Material

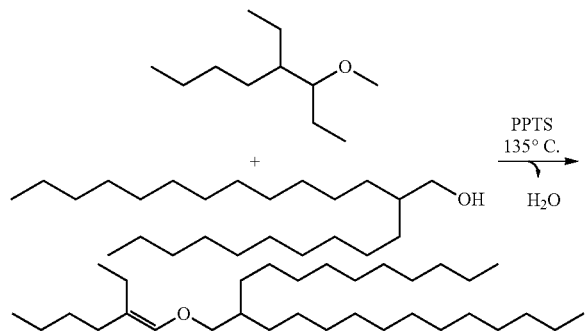

To a 3-necked round bottom flask equipped with a Dean-Stark receiver and a thermometer was added 2-decyltetradecan-1-ol (40 g, 0.11 mmol), 2-ethylhexanal dimethyl acetal (29.5 g, 0.17 mol), and pyridinium p-toluenesulfonate (0.14 g, 0.5 mol %). The reaction mixture was heated in an oil bath at 135° C. with continuous removal of methanol. After ca. 5 hr the mixture was cooled to rt overnight under N₂ before K₂CO₃ (220 mg) was added and the mixture filtered. The volatiles were removed to give a mixture comprised of 78% of the (Z)-11-(((2-ethylhex-1-en-1-yl) oxy)methyl)tricosane, 18% alcohol, <1% dehydrated alcohol (11-methylenetricosane+isomers) and 3% acetal as a colourless oil.

This comparative example demonstrates that the use of a dimethyl acetal, as opposed to a branched aldehyde, results in poorer alcohol conversion and increased by-product production when compared to Example 3, which is performed under similar conditions using the aldehyde reagent.

Example 12—Synthesis of (Z)-11-(((2-methylbut-1-en-1-yl)oxy)methyl)tricosane (Reduced Equivalents of Aldehyde)

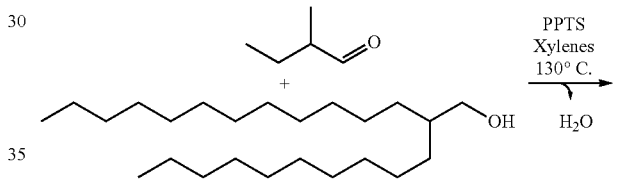

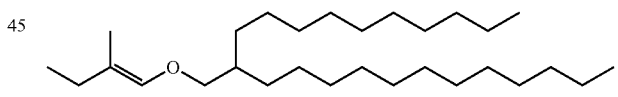

To a 3-necked round bottom flask equipped with a Dean-Stark receiver and a thermometer was added 2-decyltetradecan-1-ol (50 g, 0.14 mol), xylenes (50 g), 2-methylbutanal (36.5 g, 0.42 mol, 3 equiv.) and pyridinium p-toluenesulfonate (177 mg, 0.7 mmol, 0.5 mol %). The reaction mixture was heated in an oil bath to a temperature of 130° C. resulting in vigorous reflux. The reaction progress was monitored by GC and after ca. 5 hr the reaction was cooled to room temperature overnight under an N₂ atmosphere. K₂CO₃ (220 mg) was added and the mixture filtered. The volatiles were removed to give the (Z)-11-(((2-methylbut-1-en-1-yl)oxy)methyl)tricosane product as a yellow oil, GC analysis of the mixture: 1% dehydrated alcohol (11-methylenetricosane+isomers), 6% alcohol, 71% of the (Z)-11-(((2-methylbut-1-en-1-yl)oxy)methyl)tricosane and 20% acetal.

Comparative Example 13—Use of Linear Aldehyde 1-Octanal

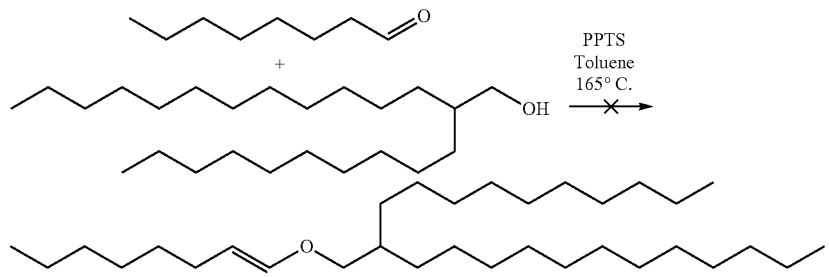

To a 3-necked round bottom flask equipped with a Dean-Stark receiver and a thermometer was added 2-decyltetradecan-1-ol (50 g, 0.14 mol), 1-octanal (50 g, 0.4 mol), toluene (30 g) and pyridinium p-toluenesulfonate (0.17 g, 0.5 mol %). The reaction mixture was heated in an oil bath at 165° C. with continuous removal of water. After ca. 4 hr the reaction mixture had turned black and GC analysis indicated the major product was derived from Aldol condensation.

This example highlights that the use of a linear aldehyde, in contrast to a branched aldehyde in accordance with the process of the present invention can lead to more unwanted Aldol condensation.

Example 14—General Procedure for Hydrogenation of Enol Ethers to Form Ethers Using H-Cube A solution of enol ether (20.27 g, 44 mmol) in heptane (400 mL, 0.1 M) was passed through a 10% Pt/C catcart (40° C., 2,000 kPa $H_2$) at 1 mL/min. The solvent was removed from the eluent under reduced pressure to yield 11-(((2-ethylhexyl)oxy)methyl)tricosane as a colourless oil (19.51 g, 96%).

Example 15—Synthesis of 11-(((2-ethylhexyl)oxy)methylene)tricosane

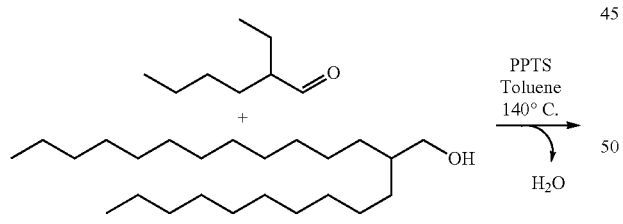

A mixture of 2-ethylhexanal (40 g, 31.3 mmol) and 2-decyltetradecan-1-ol (77.4 g, 21.9 mmol) was suspended in toluene (45 mL) and treated with pyridinium p-toluenesulfonate (120 mg). The reaction mixture was heated to an internal temperature of 140° C. and stirred under these conditions for 24 h. After this time, an additional portion of pyridinium p-toluenesulfonate (120 mg) was added and the mixture was stirred for a further 24 h at 140° C. Finally, the reaction mixture containing 11-(((2-ethylhexyl)oxy)methylene)tricosane was allowed to cool to ambient temperature and then taken forward to the hydrogenation with no purification. GC and NMR analysis of this reaction was performed to verify the effectiveness of the process of the present invention. GC analysis and NMR analysis of the crude product in heptane were both consistent with the formation of 11-(((2-ethylhexyl)oxy)methylene)tricosane with both E and Z isomers present. A peak corresponding to the enol ether alkene proton was clearly visible at 5.75 ppm in the $^1$H NMR spectrum; peaks corresponding to the two alkenyl carbons of the enol ether were clearly visible in the $^{13}$C NMR spectrum; and a peak corresponding to an alkene carbon attached directly to a proton was also clearly visible in the $^{13}$C DEPT NMR spectrum.

Examples 16, 17 and 18—Hydrogenation of 11-(((2-ethylhexyl)oxy)methylene)tricosane to form 11-(((2-ethylhexyl)oxy)methyl)tricosane

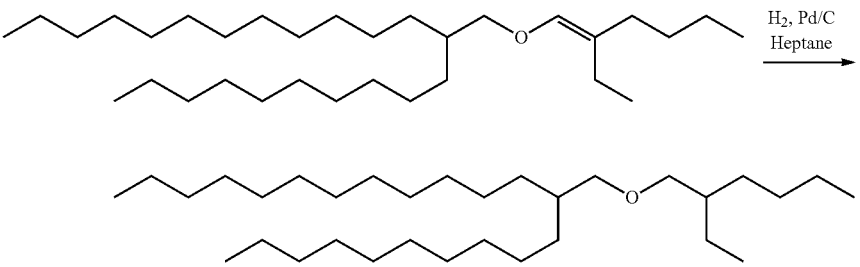

Example 16

A solution of 11-(((2-ethylhexyl)oxy)methylene)tricosane (90 g, 194 mmol) from Example 15 in heptane (1820 mL) was passed over a bed of palladium on charcoal catalyst (10 wt. % loading of palladium) (0.880 mL) at a flow rate of 1 mL/min, (LHSV of 68 h$^{-1}$), with a hydrogen flow rate of 60 mL/min at a pressure of 10,000 kPa and reaction temperature of 25° C. The conversion of enol ether to the ether product was >99%.

Example 17

A solution of 11-(((2-ethylhexyl)oxy)methylene)tricosane (90 g, 194 mmol) from Example 15 in heptane (1820 mL) was passed over a bed of palladium on charcoal catalyst (10 wt. % loading of palladium) (0.880 mL) at a flow rate of 1 mL/min, (LHSV of 68 h−1), with a hydrogen flow rate of 60 mL/min at a pressure of 500 kPa and reaction temperature of 50° C. The conversion of enol ether to the ether product was >99%.

Example 18

A solution of 11-(((2-ethylhexyl)oxy)methylene)tricosane (90 g, 194 mmol) from Example 15 in heptane (1820 mL) was passed over a bed of palladium on charcoal catalyst (10 wt. % loading of palladium) (0.880 mL) at a flow rate of 1 mL/min, (LHSV of 68 h−1), with a hydrogen flow rate of 60 mL/min at a pressure of 0 kPa and reaction temperature of 25° C. The conversion of enol ether to the ether product was >99%.

GC and NMR analysis of this reaction was performed to verify the effectiveness of the reduction. GC analysis and NMR analysis of the crude product in heptane were both consistent with the formation of 11-(((2-ethylhexyl)oxy) methyl)tricosane. GC analysis showed the saturated ether product to have one larger peak and one smaller peak, which may be attributed to the ether being present as a mixture of diastereoisomers. The $^1$H NMR and $^{13}$C NMR data confirm that there are no signals attributable to the enol ether starting material; alkenyl protons and carbons both being absent from the NMR spectra. An alternative explanation is that the smaller signal in the GC analysis is attributable to the enol ether which can be observed resulting from breakdown of a corresponding acetal on the GC injector or column. However, the evidence does not support this alternative explanation as there was no evidence for acetal by-products when the sample was analysed by NMR. Minor ester impurity was observed which results from esterification of 2-ethylhexanoic acid, which was present in the 2-ethylhexanal starting material, with 2-decyltetradecanol.

Examples 16 to 18 demonstrate that reduction is effective under very mild conditions, at both atmospheric temperature and pressure in Example 18. The yield of the reaction in this instance, when compared to the higher temperatures and pressure used in Examples 16 and 17, is identical. This highlights one advantage of the process of the present invention as high temperatures and pressures are costly to run.

Example 19—5 L Scale-Up Synthesis of (Z)-11-(((2-ethylhex-1-en-1-yl)oxy)methyl)tricosane

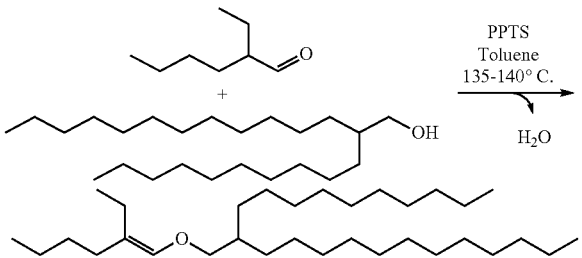

To a 5 L flange head flask equipped with an overhead stirrer, thermometer, and a Dean-Stark receiver was added 2-decyltetradecan-1-ol (1340 g, 3.8 mol), 2-ethylhexanal (1092 g, 8.5 mol, 2.2 equiv.), toluene (655 g) and pyridinium p-toluenesulfonate (4.75 g, 0.5 mol %). The reaction mixture was heated to a of 135-140° C. (vigorous reflux) with continuous removal of water (500 rpm stir speed). After 16 h of heating GC analysis of the reaction mixture indicated: 1% dehydrated alcohol (11-methylenetricosane+isomers), 20% alcohol, 67% enol ether and 10% 2-decyltetradecyl 2-ethylhexanoate (ester from 2-ethylhexanoic acid present in 2-EH feed and 2-decyltetradecan-1-01). A further equivalent of 2-ethylhexanal (413.8 g, 3.2 mol) was added to the reaction and heating continued for 16 h (GC analysis: 1% dehydrated alcohol (11-methylenetricosane+isomers), 11% alcohol, 72% enol ether and 15% 2-decyltetradecyl 2-ethylhexanoate (ester from 2-ethylhexanoic acid present in 2-EH feed and 2-decyltetradecan-1-01). The mixture was cooled to rt overnight under an N$_2$ atmosphere before K$_2$CO$_3$ (12 g) was added and the mixture filtered. The volatiles were removed to give a mixture comprised of 78% of the (Z)-11-(((2-ethylhex-1-en-1-yl)oxy)methyl)tricosane, 8% alcohol, 1% dehydrated alcohol (11-methylenetricosane+isomers) and 13% 2-decyltetradecyl 2-ethylhexanoate as a yellow oil.

This example demonstrates that the process of the present invention may be scaled up to a large extent.

Example 20—Hydrogenation of a Sample from 5 L Scale-Up Synthesis of (Z)-11-(((2-ethylhex-1-en-1-yl)oxy)methyl)tricosane

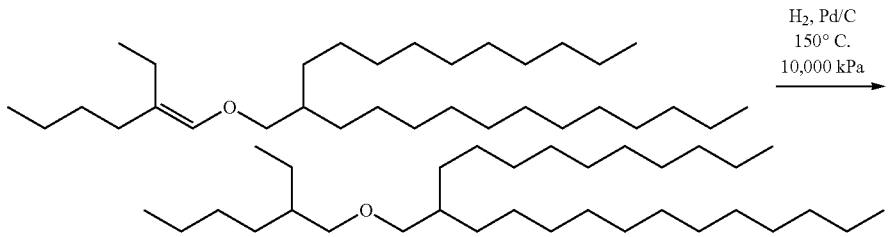

A solution of enol ether from Example 19 (9.39 g, 20 mmol) in heptane (400 mL, 0.05 M) was passed through a 10% Pd/C catcart (150° C., 10,000 kPa H$_2$) at 0.8 mL/min. The solvent was removed from the eluent under reduced pressure to yield a mixture of 75% 11-(((2-ethylhexyl)oxy) methyl)tricosane, 7% alcohol, 16% 2-decyltetradecyl 2-ethylhexanoate and 1% 11-methyltricosane as a colourless oil (8.01 g).

This example demonstrates that reduction may be performed on a large scale.

Comparative Example 21 Preparation of 11-(((2-ethylhexyl)oxy)methyl)tricosane Via the Acetal Synthesis of the Acetal Precursor

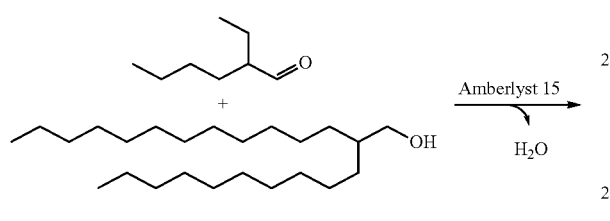

A solution of 2-ethylhexanal (5.0 g, 0.039 mol) and 2-decyltetradecan-1-ol (35 g, 0.098 mol) was treated with Amberlyst 15 resin (200 mg (dry mass), pre-washed in deionised water and dried) and 4 Å molecular sieves (0.7 g, activated at 145° C. for >48 h) and stirred at rt for 24 h. Next the reaction mixture was filtered through celite to remove the Amberlyst 15 catalyst and molecular sieve. The crude acetal was purified on silica using heptane as the eluent to provide the acetal (12.7 g, 0.016 mol, 40% yield) as a colourless oil.

Hydrogenolysis of the Acetal to the Corresponding Ether

A solution of the acetal (11 g, 0.013 mol) in toluene (20 mL) was hydrogenated at a temperature of 135° C. and a pressure of 10,000 kPa over a palladium on charcoal (10 wt. % loading of palladium) to give the 11-(((2-ethylhexyl)oxy) methyl)tricosane ether as a 1:1 molar mixture in 2-decyltetradecan-1-ol. The crude ether was purified on silica using heptane as the eluent to provide the ether (5.8 g, 0.012 mol, 92% yield) as a colourless oil.

Comparative Example 22—Preparation of 11-((2-methylbutoxy)methyl)tricosane Via the Acetal Synthesis of the Acetal Precursor

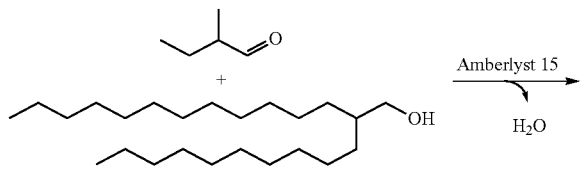

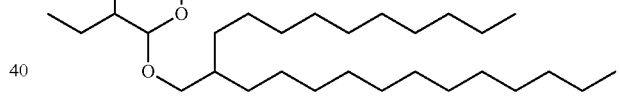

A solution of 2-methylbutanal (30 g, 0.39 mol) and 2-decyltetradecan-1-ol (308 g, 0.87 mol) was passed over a bed of Amberlyst 15 resin (10 mL, bed, LHSV=60 h−1) and a separate bed of activated mg 4 Å molecular sieves (10 mL, bed, LHSV=60 h−1). The crude product was distilled at a pressure of 1 mbar and a temperature of 210° C., to leave the acetal (190 g, 0.24 mol, 63% yield) as a colourless oil.

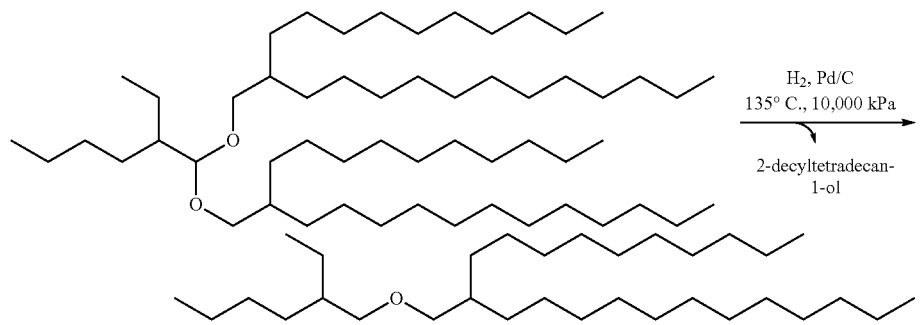

Hydrogenolysis of the Acetal to the Corresponding Ether

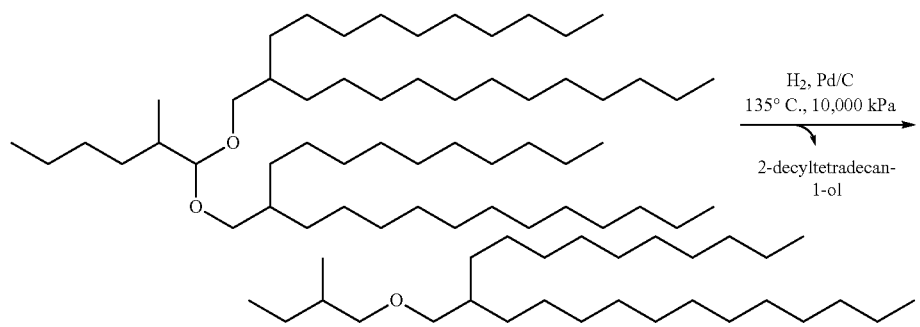

A solution of the acetal (40 g, 0.051 mol) in toluene (500 mL) was hydrogenated at a temperature of 135° C. and a pressure of 10,000 kPa over a palladium on charcoal catalyst (10% wt loading of palladium) to give the 11-((2-methylbutoxy)methyl)tricosane ether as a 1:1 molar mixture in 2-decyltetradecan-1-ol. The crude ether was purified on silica using heptane as the eluent to provide the ether (19.4 g, 0.046 mol, 90% yield) as a colourless oil.

Comparative Example 23—Preparation of 11-((pentyloxy)methyl)tricosane Via the Acetal Synthesis of the Acetal Precursor

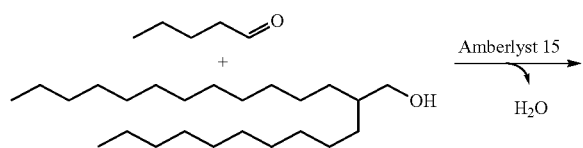

A solution of 1-pentanal (30 g, 0.39 mol) and 2-decyltetradecan-1-ol (308 g, 0.87 mol) was passed over a bed of Amberlyst 15 resin (10 mL, bed, LHSV=60 h−1) and a separate bed of activated mg 4 Å molecular sieves (10 mL, bed, LHSV=60 h−1). The crude product was distilled at a pressure of 1 mbar and a temperature of 210° C., to leave the acetal (170 g, 0.22 mol, 56% yield) as a colourless oil.

Hydrogenolysis of the Acetal to the Corresponding Ether

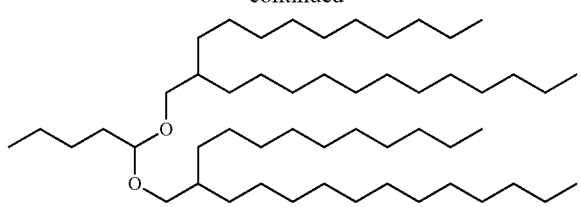

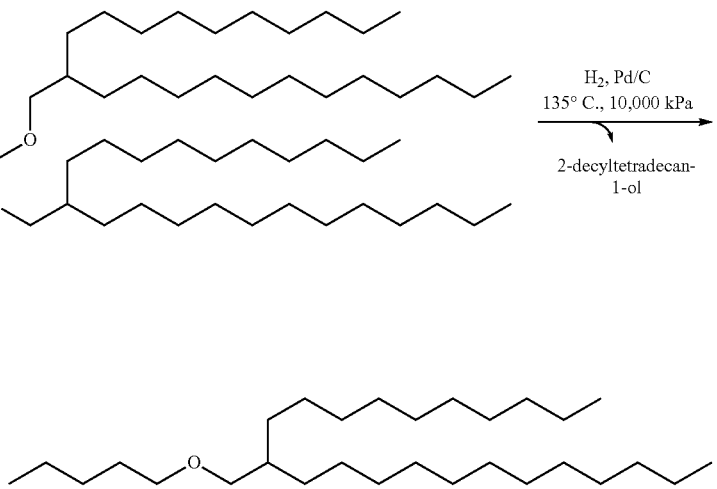

A solution of the acetal (40 g, 0.051 mol) in toluene (500 mL) was hydrogenated at a temperature of 135° C. and a pressure of 10,000 kPa over a palladium on charcoal catalyst (10% wt loading of palladium) to give the 11-((pentyloxy)methyl)tricosane ether as a 1:1 molar mixture in 2-decyltetradecan-1-ol. The crude ether was purified on silica using heptane as the eluent to provide the ether (20.9 g, 0.049 mol, 97% yield) as a colourless oil.

Comparative Example 24—Preparation of 11-((isopentyloxy)methyl)tricosane Via the Acetal Synthesis of the Acetal Precursor

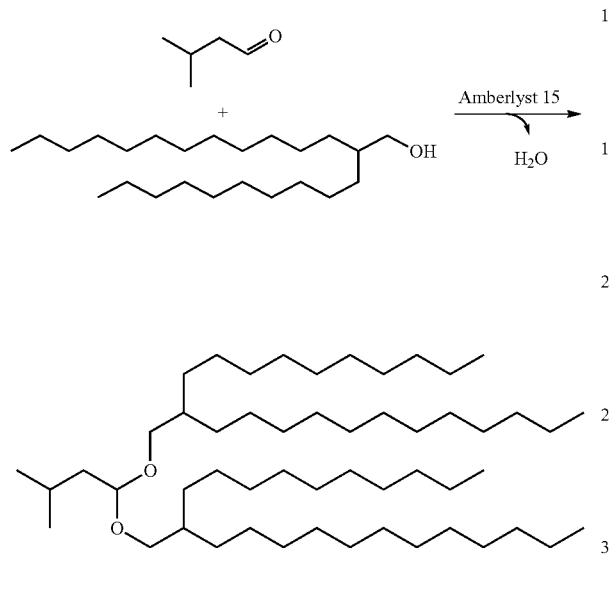

A solution of 1-pentanal (30 g, 0.39 mol) and 2-decyltetradecan-1-ol (308 g, 0.87 mol) was passed over a bed of Amberlyst 15 resin (10 mL, bed, LHSV=60 h−1) and a separate bed of activated mg 4 Å molecular sieves (10 mL, bed, LHSV=60 h−1). The crude product was distilled at a pressure of 1 mbar and a temperature of 210° C., to leave the acetal (194 g, 0.25 mol, 65% yield) as a colourless oil.

Hydrogenolysis of the Acetal to the Corresponding Ether

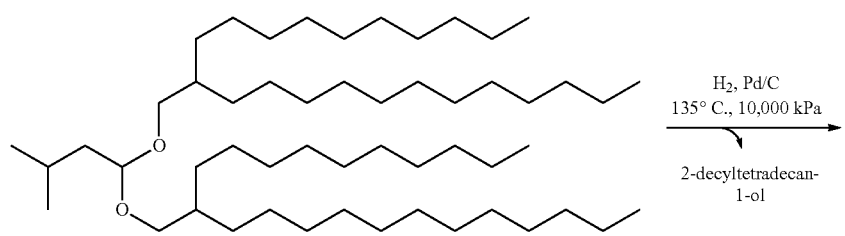

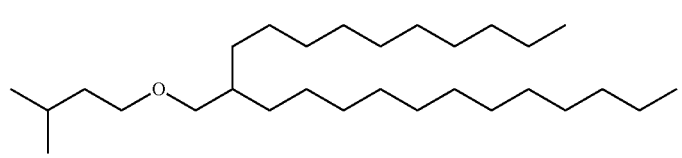

A solution of the acetal (40 g, 0.051 mol) in toluene (500 mL) was hydrogenated at a temperature of 135° C. and a pressure of 10,000 kPa over a palladium on charcoal catalyst (10% wt loading of palladium) to give the 11-((isopentyloxy)methyl)tricosane ether as a 1:1 molar mixture in 2-decyltetradecan-1-ol. The crude ether was purified on silica using heptane as the eluent to provide the ether (18.1 g, 0.043 mol, 84% yield) as a colourless oil.

Comparative Example 25—Preparation of 11-((2-methylbutoxy)methyl)tricosane from 2-decyl-1-tetradecanal Via the Acetal Synthesis of the Acetal Precursor

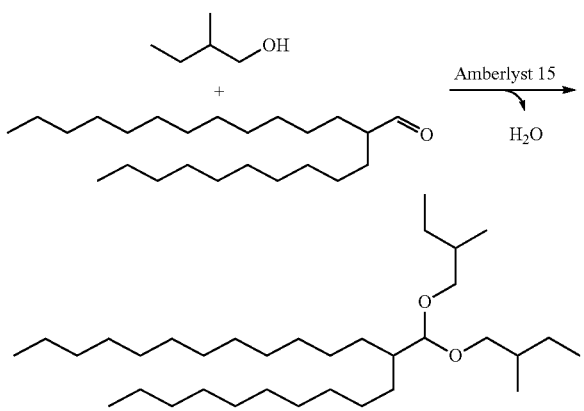

A solution of 2-decyl-1-tetradecanal (20 g, 0.057 mol) and 2-methylbutan-1-ol (88 g, 1 mol) was passed over a bed of Amberlyst 15 resin (10 mL, bed, LHSV=60 h−1) and a separate bed of activated 4 Å molecular sieves (10 mL, bed, LHSV=60 h−1). The crude product was purified on silica using heptane as the eluent to give the acetal (19.8 g, 0.039 mmol, 68% yield) as a colourless oil.

Hydrogenolysis of the Acetal to the Corresponding Ether

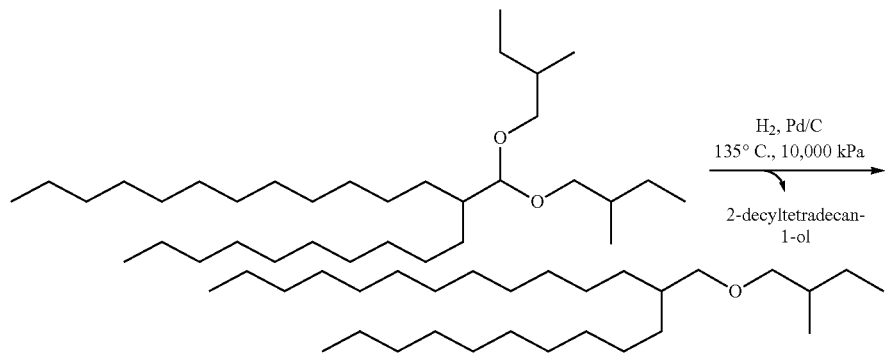

A solution of the acetal (19 g, 0.037 mol) in toluene (300 mL) was hydrogenated at a temperature of 135° C. and a pressure of 10,000 kPa over a palladium on charcoal (10 wt. % loading of palladium) to give 11-((2-methylbutoxy)methyl)tricosane as a 1:1 molar mixture in 2-methylbutan-1-ol. The crude ether was purified in vacuo, to remove residual 2-methylbutan-1-ol, to provide the ether (13.8 g, 0.033 mmol, 88% yield) as a colourless oil.

Examples 21 to 25 demonstrate comparative reactions performed via acetal formation and producing the same ethers as those formed in previous examples according to the present invention. These examples demonstrate that higher pressures and temperatures are required to reduce the acetals to the desired ethers as opposed to the enol ethers produced according to the present invention. This highlights the advantages of the present invention as the high temperatures and pressures are costly.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope and spirit of this invention.

The invention claimed is:

1. A process for preparing an enol ether comprising the steps of:

i) contacting a branched-chain aldehyde having the formula (II):

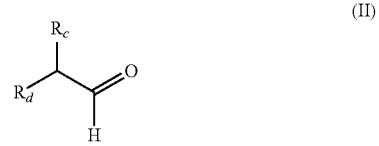

wherein $R_c$ and $R_d$ are independently selected from $C_1$ to $C_{18}$ alkyl with a branched-chain alcohol having the formula (I):

wherein $R_a$ and $R_b$ are independently selected from $C_1$ to $C_{18}$ in the presence of an acid catalyst and a solvent to form a reaction mixture, wherein the solvent is selected from the group consisting of xylenes, toluene, ethylbenzene, chlorobenzene, and mixtures thereof; and ii) heating the reaction mixture formed in step i) under reflux with continuous removal of water by-product, wherein the reaction temperature in step ii) is greater than about 125° C. and less than about 170° C.

2. The process of claim 1, wherein solvent removed from the reaction mixture as part of the continuous water by-product removal in step ii) is separated and recycled to the reaction mixture.

3. The process of claim 1, wherein the alcohol is 2-decyltetradecan-1-ol or 2-octyldodecan-1-ol.

4. The process of claim 1, wherein the aldehyde is 2-ethylhexanal, 2-methylbutanal, 2-methylpropanal, 2-ethylbutanal or 2-propylheptanal.

5. The process of claim 1, wherein a molar excess of aldehyde is used.

6. A process for preparing an enol ether comprising the steps of:

i) contacting a branched-chain aldehyde having the formula (II):

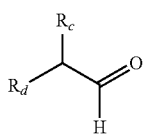

wherein $R_c$ and $R_d$ are independently selected from $C_1$ to $C_{18}$ alkyl with a branched-chain alcohol having the formula (I):

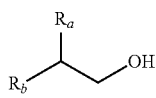

wherein $R_a$ and $R_b$ are independently selected from $C_1$ to $C_{18}$ in the presence of a catalyst and a solvent to form a reaction mixture, wherein and the solvent is selected from the group consisting of xylenes, toluene, ethylbenzene, chlorobenzene, and mixtures thereof; and ii) heating the reaction mixture formed in step i) under reflux with continuous removal of water by-product, wherein the reaction temperature in step ii) is greater than about 125° C. and less than about 170° C., and wherein the catalyst is a weak acidic salt comprising a pyridinium, collidinium or lutidinium cation and/or a p-toluenesulfanate anion or an alkali metal or an alkaline earth metal cation and a hydrogensulfonate anion.

7. The process of claim 6, wherein the weak acid salt is formed in situ during step i).

8. The process of claim 1, wherein the catalyst is selected from p-toluenesulfonic acid, sulfuric acid, potassium bisulfate, sodium bisulfate, potassium ($C_1$-$C_8$-alkyl)sulfonate, ($C_1$-$C_8$-alkyl)sulfonic acids, benzene sulfonic acid, methylsulfonic acid, N—($C_1$-$C_8$-alkyl)sulfamic acids, N,N-di($C_1$-$C_8$-alkyl)sulfamic acids, hydrochloric acid, phosphoric acid, ammonium nitrate, potassium bisulfate, cerium (III) chloride, iron (III) chloride, scandium(III) trifluoromethanesulfonimide, aluminium trifluoromethanesulfonate, bismuth trifluoromethanesulfonate, tetrabutylammonium tribromide, N-bromosuccinimide, N,N'-bis[3,5-bis(trifloro-methyl)phenyl]thiourea, an acidic ion-exchange resin, an aluminosilicate etherification catalyst and a zeolite.

9. The process of claim 1, wherein the reaction temperature in step ii) is from about 125° C. to about 165° C.

10. The process of claim 1, wherein the enol ether formed in the process has a total number of carbon atoms of from 20 to 60.

11. The process of claim 1, further comprising the step of:
iii) reducing the enol ether obtained from step ii) to form a saturated ether.

12. The process of claim 11, wherein the step of reducing in step iii) is hydrogenation and is performed in the presence of a hydrogenation catalyst.

13. The process of claim 11, wherein reduction in step iii) is conducted at a temperature in the range of from about 0° C. to about 350° C. and at a pressure of from atmospheric pressure to about 30,000 kPa absolute.

14. A process for preparing a lubricant composition, the process comprising
   i) preparing an enol ether according to the process of claim 1;
   (ii) reducing the enol ether to form a saturated ether; and
   (iii) blending the saturated ether into a lubricant composition.

15. A process for lubricating a surface, the process comprising
   (i) preparing an lubricant composition according to the process of claim 14;
   (ii) reducing the enol ether to form a saturated ether;
   (iii) blending the saturated ether into a lubricant composition; and
   (iv) supplying the lubricant composition to the surface.

* * * * *